United States Patent
Mikaelian

(10) Patent No.: US 10,219,693 B2
(45) Date of Patent: Mar. 5, 2019

(54) SYSTEMS AND METHODS FOR COMBINED STRUCTURE AND FUNCTION EVALUATION OF RETINA

(71) Applicants: NIDEK CO., LTD., Aichi (JP); Gareguin Mikaelian, Fremont, CA (US)

(72) Inventor: Gareguin Mikaelian, San Pedro, CA (US)

(73) Assignee: NIDEK CO., LTD., Aichi (JP)

(*) Notice: Subject to any disclaimer, the term of this patent is extended or adjusted under 35 U.S.C. 154(b) by 0 days.

(21) Appl. No.: 15/556,313

(22) PCT Filed: Mar. 11, 2016

(86) PCT No.: PCT/US2016/022109
§ 371 (c)(1),
(2) Date: Sep. 7, 2017

(87) PCT Pub. No.: WO2016/145367
PCT Pub. Date: Sep. 15, 2016

(65) Prior Publication Data
US 2018/0070814 A1    Mar. 15, 2018

Related U.S. Application Data

(60) Provisional application No. 62/132,118, filed on Mar. 12, 2015.

(51) Int. Cl.
*A61B 3/10* (2006.01)
*A61B 3/024* (2006.01)
(Continued)

(52) U.S. Cl.
CPC .............. *A61B 3/102* (2013.01); *A61B 3/024* (2013.01); *A61B 3/1025* (2013.01); *A61B 3/06* (2013.01);
(Continued)

(58) Field of Classification Search
CPC .. A61B 3/14; A61B 3/102; A61B 3/12; A61B 3/0025; G01B 9/02091
(Continued)

(56) References Cited

U.S. PATENT DOCUMENTS 5,568,208 A * 10/1996 Van de Velde ...... A61B 3/1025
351/205
6,290,357 B1 * 9/2001 Massengill ............ A61B 3/024
351/209
(Continued)

*Primary Examiner* — Mohammed A Hasan
(74) *Attorney, Agent, or Firm* — Rankin, Hill & Clark LLP

(57) ABSTRACT

According to one or more embodiments, systems and methods that combine structural examination capabilities of one device with functional examination capabilities of another device to perform a separate or combined structural and functional evaluation of visual functions of the patient's eyes are described herein. A system for combined structural and functional evaluation of a retina may include a structural evaluation unit which may be an OCT, PS-OCT, SLO or PS-SLO and a functional evaluation unit which may be a perimeter, microperimeter, or any other type of visual field analyzer. The structural evaluation unit and the functional evaluation unit may be located within a same housing, and thus may be utilized as a single device. The structural evaluation unit may record structural measurements associated with the patient's eye or retina and the functional evaluation unit may record functional measurements associated with the patient's field of view.

18 Claims, 15 Drawing Sheets

(51) Int. Cl.
    *A61B 3/06*    (2006.01)
    *A61B 3/113*   (2006.01)
    *A61B 3/12*    (2006.01)
    *A61B 3/14*    (2006.01)

(52) U.S. Cl.
    CPC ............. *A61B 3/113* (2013.01); *A61B 3/12* (2013.01); *A61B 3/14* (2013.01)

(58) Field of Classification Search
    USPC ........................................................ 351/206
    See application file for complete search history.

(56) References Cited

U.S. PATENT DOCUMENTS 8,049,899 B2 *  11/2011  Waelti ................... A61B 3/102
                                                                356/497
2009/0141240 A1 *  6/2009  Weitz ................... G01B 9/0203
                                                                351/246

* cited by examiner

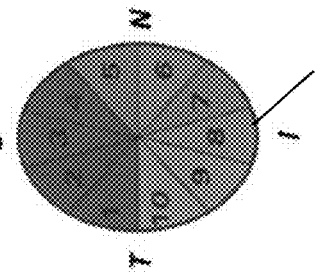
FIG. 3C Prior Art  ONH Sectors
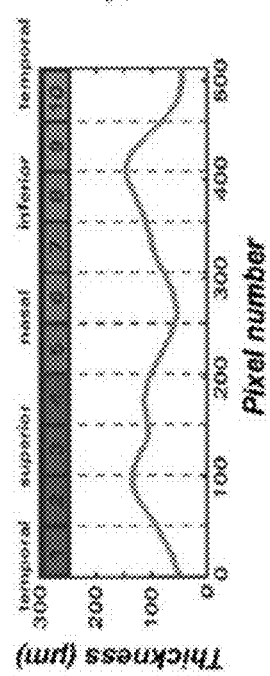
FIG. 3B Prior Art  OCT Sectors
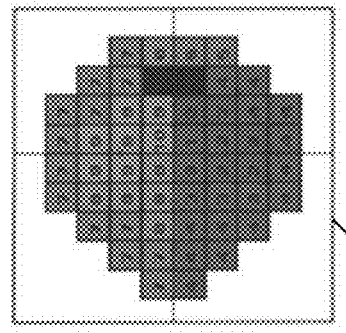
FIG. 3A Prior Art  Visual Field Locations
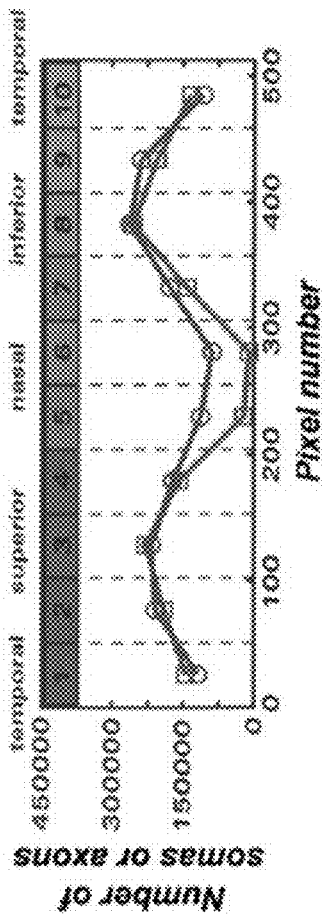
FIG. 3D Prior Art  Cell counts from normative SAP and OCT data for 40 monkey eyes.
SAP: 1,458,416 total RGCs
OCT: 1,500,004 total axons

SYSTEMS AND METHODS FOR COMBINED STRUCTURE AND FUNCTION EVALUATION OF RETINA

CROSS-REFERENCE TO RELATED APPLICATIONS

This application claims the benefit of U.S. Provisional Patent Application, Ser. No. 62/132,118 entitled "SYSTEMS AND METHODS FOR COMBINED STRUCTURE AND FUNCTION EVALUATION OF RETINA", filed on Mar. 12, 2015; the entirety of the above-noted application(s) is incorporated by reference herein.

TECHNICAL FIELD

The present disclosure relates to advanced diagnostics of ocular diseases using Optical Coherence Tomography (OCT).

BACKGROUND

The Humphrey Field Analyzer (HFA) is a visual field testing tool or apparatus which may be used for measuring the visual field of a patient and is widely used in visual field testing. The HFA includes a large dome-shaped screen and a projection system, and is configured to evaluate the ability of the patient to recognize visual stimuli at a large range of relative intensities, stimuli sizes, and field angles. One of the standard HFA programs, the 24-2, has become a useful tool for diagnosis of glaucoma and determination of the disease progression rate.

However, because the HFA was developed decades ago, drawbacks exist. For example, the HFA utilizes a primitive eye tracking device which makes it difficult to pinpoint the exact location of stimulus on a retina of the patient, thereby causing registration of the stimulus to a point on the retina to be slower or inaccurate.

Since its introduction to ophthalmology, OCT has become a widely used diagnostic tool for visualizing a structure of the retina and distinguishing between different retinal layers of the retina of the patient. For example, the OCT may be used to take structural measurements of optic nerve head, retinal nerve fiber layer (RNFL), or [NFL (nerve fiber layer)+GCL (ganglion cell layer)+IPL (inner plexiform layer)] thicknesses. These structural measurements or thicknesses may be utilized for early and diagnostics of glaucoma and its progression.

BRIEF DESCRIPTION

According to one aspect, a device for performing combined structure and function evaluation of a retina of a patient includes a functional evaluation unit performing a visual examination by providing a visual stimulus to the retina and recording a reaction of the patient and a structural evaluation unit recording one or more structural measurements associated with the retina of the patient.

The functional evaluation unit may be a perimeter, a visual field analyzer, or a microperimeter. The structural evaluation unit may be an optical coherence tomography (OCT) unit, a polarization sensitive optical coherence tomography (PS-OCT) unit, a scanning laser ophthalmoscope (SLO) unit, or a polarization sensitive scanning laser ophthalmoscope (PS-SLO).

The functional evaluation unit may include a gaze tracking system having two or more imaging sensors, such as an infrared camera or an anterior segment camera. The structural evaluation unit may record one or more retinal layer thicknesses, determine an orientation of retinal nerve fiber layer (RNFL) bundles or RNFL capacity. The functional evaluation unit may provide the visual stimulus to the retina based on one or more of the structural measurements taken by the structural evaluation unit. The structural evaluation unit may record one or more of the structural measurements based on the reaction of the patient to the visual stimulus.

In one or more embodiments, the functional evaluation unit may provide the visual stimulus to the retina based on an orientation of the RNFL bundles and previous responses from the patient to determine one or more scotoma boundaries. The functional evaluation unit may determine progression of scotomas based on an area of a scotoma and movement of one or more of the scotoma boundaries. During the visual examination, the functional evaluation unit may project a fixation gaze target onto both eyes of the patient and the visual stimuli onto merely one of the eyes of the patient at a time. The fixation gaze on the eye where stimuli is not projected may appear on a dark background. Positions of fixation gaze targets projected onto both eyes may be coordinated such that both eyes are looking in a same direction.

According to one aspect, a method for performing combined structure and function evaluation of a retina of a patient may include performing a visual examination using a functional evaluation unit of a device which provides a visual stimulus to the retina and records a reaction of the patient and recording one or more structural measurements using a structural evaluation unit of the same device, the structural measurements associated with the retina of the patient.

The functional evaluation unit is a perimeter, a visual field analyzer, or a microperimeter. The structural evaluation unit is an optical coherence tomography (OCT) unit, a polarization sensitive optical coherence tomography (PS-OCT) unit, a scanning laser ophthalmoscope (SLO) unit, or a polarization sensitive scanning laser ophthalmoscope (PS-SLO). The method may include tracking eyes of the patient using a retinal tracking system and an anterior segment tracking system or comparing one or more of the structural measurements with measurements from a database indicative of healthy structural measurements.

According to one or more aspect, a device for performing combined structure and function evaluation of a retina of a patient may include a functional evaluation unit performing a visual examination by providing a visual stimulus to the retina and recording a reaction of the patient, a structural evaluation unit recording one or more structural measurements associated with the retina of the patient, and a gaze tracking system imaging and tracking the retina and registering a location of the visual stimulus on the retina.

BRIEF DESCRIPTION OF THE DRAWINGS

FIG. 3 is an illustration of an example spatial relationship map for a retina, according to one or more embodiments.

DETAILED DESCRIPTION

Figure 1:
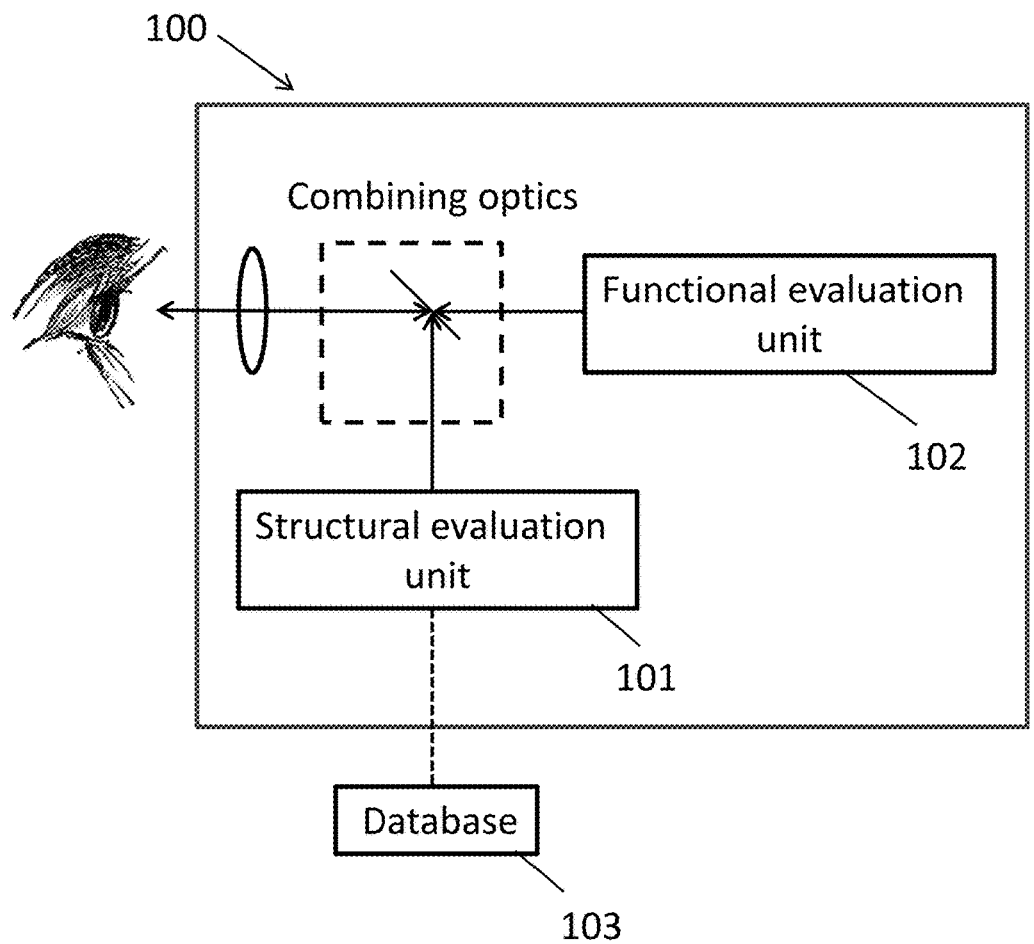
FIG. 1 is an illustration of an example block diagram of a system for combined structural and functional evaluation of a retina, according to one or more embodiments.

Problems to be Solved by the Invention

The present disclosure is directed towards systems and methods for performing accurate evaluation of the eye, including structural or functional characteristics or both.

Traditionally, functional evaluation of the retina is performed using perimeters, such as the HFA. Most perimeters are fairly straight-forward to operate and provide information about retina sensitivity at different locations across the retina. During a perimetry examination, the patient is instructed to look at a certain fixation point and to press a button every time he or she detects a visual stimulus. The eye may be tracked with an eye tracker, and if the gaze direction deviates significantly from the desired direction, the particular data point in the measurement may be omitted or re-measured. Such method for measuring the visual field is inherently inaccurate in terms of registration of the visual field test location with the exact location on the retina. To address this issue, the concept of microperimetry was developed, where a real time image of the retina is analyzed simultaneously with the visual field examination, and an accurate location of the presentation of the stimulus on the retina may be achieved.

In recent years, since the wide adoption of OCT technology in ophthalmological diagnostics, a significant interest has been focused towards relationships between structural and functional aspects of the retina. For example, in the case of glaucoma, it was demonstrated that the disease is generally accompanied by both a reduction of a visual field and a thinning of retina nerve fiber layer (RNFL) and/or the thinning of the [NFL+GCL+IPL] layers. However, the relationship between the visual field and retinal layer thickness may be fairly complex. In some cases, the structural change appears before the functional change, while in other cases the change in the visual field precedes any measurable changes in the structure of the retina. Therefore, for accurate diagnostics of many eye diseases, such as glaucoma, it may be advantageous to simultaneously assess structural and functional changes in the retina.

Currently, structural and functional changes in the retina are assessed by performing a functional examination using a first device and a structural examination using a second device. In other words, the assessment of the structural and functional changes in the retina is performed by combining the examination from two devices, where the functional examination is performed using a perimeter, visual field analyzer, or a microperimeter, and the functional evaluation is performed using an OCT, and the data from the two devices is registered using a fundus image or by matching the blind spot in the visual field to the location of the optic nerve. In this way, the measurements from the two different devices are individually registered to an image of the fundus and the registration and analysis of the structure and function is performed on a separate device. While this may be suitable for research applications, it may be cumbersome in a clinical setting.

Additionally, it may be desirable to shorten examination time for one or both procedures. One of the challenges in conducting a functional examination is the time required to conduct a comprehensive exam. For example, the examination typically used for visual field testing is the 24-2 program employed in the HFA. It assesses the visual field threshold values at 54 different points on the retina. While a SITA-FAST threshold algorithm may be used, the examination time may still last up to several minutes and be tiresome for both the operator and the patient. This is problematic when attempting to use the instrument as a screening device where a high throughput is desired. In this regard, shortening the visual field examination time may be a desirable feature that will allow visual field examination to be used for rapid screening of patients for various conditions.

Means of Solving the Problems

Because research has indicated that there are relationships between structural and functional components of a patient's eye, these relationships may be utilized for early diagnosis and better characterization of ocular diseases, an associated disease stage, and progression of the disease. Provided herein are systems and techniques for combined structure and function evaluation of the retina.

According to one or more aspects, advanced diagnostics of ocular diseases may be provided by combining visual field testing and structural evaluation of the retina, such as with Optical Coherence Tomography (OCT) or polarization sensitive scanning laser ophthalmoscope (PS-SLO). In other words, systems and methods for combined testing of the visual field and structural measurements of the retina are provided herein. For example, information about a glaucoma or more accurate diagnostics of a disease may be provided by combining the functional information obtained with a visual field testing apparatus and the structural information obtained with the OCT using a single device which would enable simultaneous or concurrent evaluation of the visual field and retinal structure of a patient's eye(s).

Thus, the present disclosure provides for systems and methods that combine structural examination capabilities of one device with functional examination capabilities of another device to perform a separate or combined structural and functional evaluation of visual functions of the patient's eyes.

FIG. 1 is an illustration of an example block diagram of a system 100 for combined structural and functional evaluation of a retina, according to one or more embodiments. The system 100 may include a structural evaluation unit 101 which may be an OCT, PS-OCT, SLO, PS-SLO or any other type of device capable of structural evaluation of the retina and a functional evaluation unit 102 which may be a perimeter, microperimeter, or any other type of visual field analyzer. The structural evaluation unit 101 and the functional evaluation unit 102 may be located within a same housing, and thus the two units 101 and 102 may be utilized as a single device. The structural evaluation unit 101 may record structural measurements associated with the patient's eye or retina and the functional evaluation unit 102 may record functional measurements associated with the patient's field of view.

Further, the structural evaluation unit 101 and the functional evaluation unit 102 of FIG. 1 may conduct or record structural and functional measurements in a simultaneous or consecutive fashion. Thus, the system 100 may provide a more efficient evaluation of the visual field and retinal structure of the patient's eye.

In one or more embodiments, the structural evaluation unit 101 first performs the structural evaluation of the patient's retina and the functional evaluation unit 102 may modify the functional exam to test specific locations on the retina that were determined to be suspect locations for scotoma based on results from the structural evaluation. For example, the structural evaluation unit 101 may analyze the thickness of certain retinal layers at various locations on the retina of the patient and compare those measurements to a database 103 associated with 'normal' patient measurements (e.g., the typical thickness of certain retinal layers at various locations across an 'average' eye or an age-corrected 'average' eye).

In another embodiment, retinal layer thicknesses at different locations may be compared to detect abnormal or suspect regions (e.g., variation across thicknesses in the different regions of the patient's eye). For example, information about RNFL thickness and birefringence at a plurality of different locations or regions on the retina may be compared to each other to determine localized ganglion cell loss.

In one or more embodiments, the database 103 may include maps derived from a prior knowledge of anatomy. In this regard, the structural evaluation unit 101 may assign a correspondence map between locations on the retina with the regions or locations around the optic nerve head. These correspondence maps may be based on anatomic studies performed on non-human primates, human primates, humans, or on empirical determination of structure-function relationships done from the analysis of a plurality of human subject data.

In other embodiments, the anatomy of the subject or patient may be evaluated by the structural evaluation unit 101 in order to compute or estimate the correspondence map for the individual subject (e.g., without using database 103). For example, a spatially resolved map of the orientation angle of ganglion cell axons may be used to compute or estimate the correspondence map between a point or region on the retina and a corresponding point or region around the optic nerve head.

Further, the structural evaluation may be presented to a healthcare professional who, based on the evaluation, may assign specific locations of interest for functional evaluation (e.g., by the functional evaluation unit 102) of the visual function.

In one or more embodiments, such function may be implemented using two separate devices and registering results of the functional and structural evaluation by comparing and registering respective fundus images recorded by the two separate devices. In other embodiments, the evaluation may be performed on a single device and the registration may come from an intrinsic alignment of the structural and functional modules (e.g., structural evaluation unit 101 and functional evaluation unit 102) within the device (e.g., system 100).

Further, the structural evaluation unit 101 may be utilized to facilitate functional testing by the functional evaluation unit 102. For example, the structural evaluation unit 101 may be a scanning laser ophthalmoscope (SLO), which may be used to track the position of the retina during the visual field examination conducted by the functional evaluation unit 102. As another example, a fundus camera unit may be used to track the position of the retina during the visual field examination.

Regardless, the structural evaluation or functional examination may be recorded before, simultaneously, concurrently, or after the visual field examination. As such, the operational wavelength of the functional examination unit may be outside the visible range of the human eye or may be within the visible range of the eye and may be part of the background illumination for the functional evaluation unit 102 (e.g., perimeter unit).

The structural evaluation unit 101 may take measurements associated with indications of glaucoma. For example, glaucoma is related to the ganglion cell loss and may manifest itself in thinning of the RNFL. In general, the RNFL includes ganglion cell axons and other supportive structure, such as glial cells and Muller cells. Ganglion cell axons are directional and when imaged with polarization sensitive imaging techniques, may show birefringence. The amount of birefringence may be correlated to the thickness of the RNFL. However, such measurements do not take into account the thickness of the supporting non-birefringent structure of the RNFL. In this regard, the structural evaluation unit 101 may record or obtain information about birefringence in the RNFL together with the information about the actual thickness of the RNFL. In this way, a relative loss of birefringence with respect to the actual RNFL thickness may be utilized to indicate abnormality and ganglion cell loss, and possibly, glaucoma.

As another example, glaucoma may be related to an iridocorneal angle, which may also be measured by the structural evaluation unit 101, such as with an anterior segment OCT, which may include an optical attachment for obtaining measurements associated with the anterior segment of the eye (e.g., iridocorneal angle measurements).

As discussed, the structural evaluation unit 101 which may be an OCT, PS-OCT, SLO, or PS-SLO and may measure information about the actual RNFL, RNFL thickness, RNFL birefringence, etc. Thus, different variations or embodiments of measurements may be implemented. For example, information about the actual RNFL may be measured using an OCT, while the RNFL birefringence may be measured using polarization sensitive SLO, adaptive optics polarization sensitive SLO, polarization sensitive OCT, etc.

In one or more embodiments, the functional evaluation unit 102 may be used to perform a short wavelength automated perimetry (SWAP) examination or a frequency doubling perimetry examination. In one or more embodiments, brightness of the presented stimuli may be less than the brightness of the background on which they are presented.

Continuing on with FIG. 1, the functional evaluation unit 102 may include a visual field testing unit providing a visual stimulus to the retina and recording the patient's reaction. Similarly, the structural evaluation unit 101 may include an OCT unit assessing structural information associated with the patient's retina. The OCT unit may measure the thickness of the RNFL in a plurality of locations on the retina including, but not limited to the peripapillary region of the optic nerve head.

Figure 2:
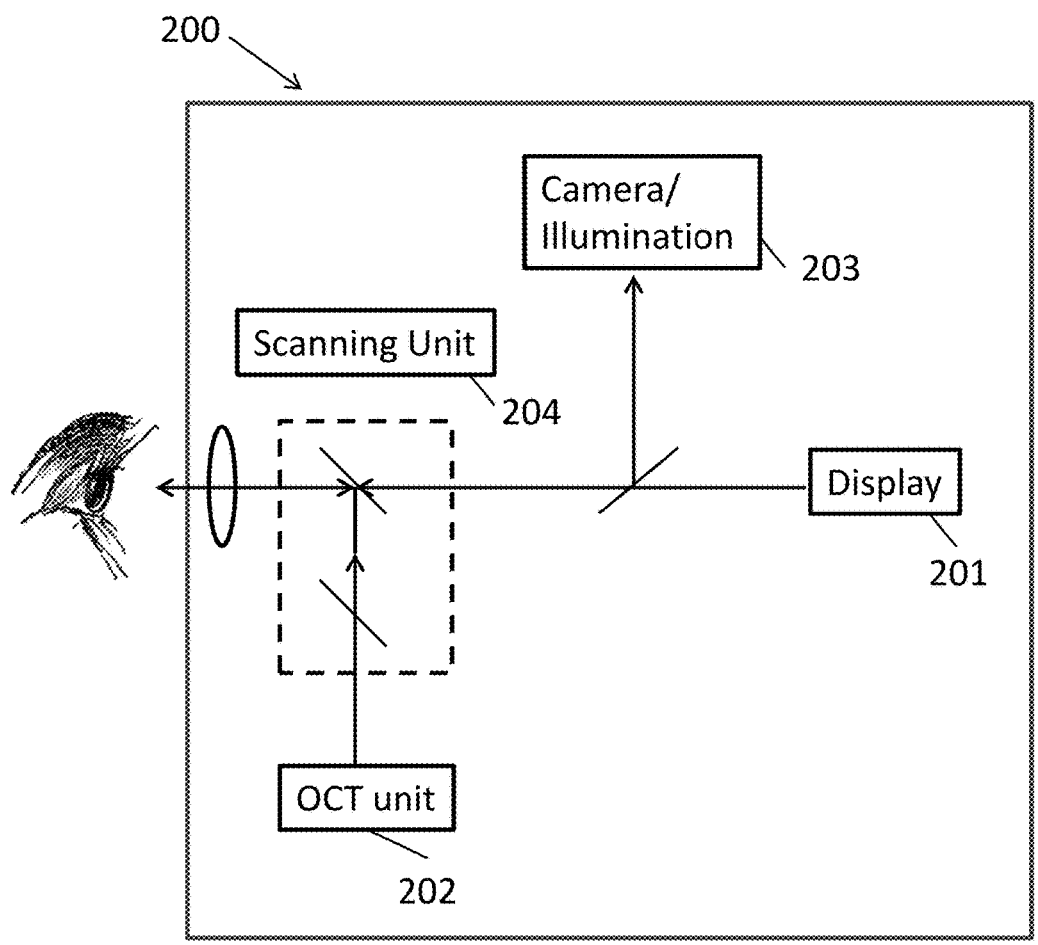
FIG. 2 is an illustration of an example block diagram of a system for combined structural and functional evaluation of a retina, according to one or more embodiments.

FIG. 2 is an illustration of an example block diagram of a system 200 for combined structural and functional evaluation of a retina, according to one or more embodiments. The system 200 may include a display 201, an OCT unit 202, a camera 203, and optics 204. The display 201 is configured to present visual stimuli during functional evaluation. The OCT unit 202 is configured to perform structural evaluation of the retina. The camera 203 is configured to perform real time retina tracking during the examination. The camera 203 may include an illumination module having an illumination source which may provide infrared (IR) light, for example. The front end optics 204 may be the same for both the OCT unit 202 and the visual field testing apparatus (e.g., 102 of system 100 or the camera 203 and display 201). Thus, the patient's eye may be positioned in front of the system 200, which acts as a single device performing both the OCT and the visual field examination.

As previously discussed, the OCT unit 202 performs structural evaluation on a patient's eye, such as by recording structural measurements associated with the patient's eye or retina. However, other components or units may be substituted for the OCT unit 202 of FIG. 2, such as a PS-OCT, SLO, PS-SLO, or any other device that may be used for structural evaluation of the retina. Similarly, the display 201 may be interchangeably replaced with different types of displays, such as an LCD, LED, DMD, LCoS, or any other type of display.

Embodiments of systems or techniques disclosed herein, or aspects thereof may provide a set of possible solutions that may be implemented together or independently to address one or more of the above challenges. The information obtained from the visual field examination and the structural information (e.g., from the OCT) may be used independently or together in order to evaluate the patient's state of disease, progression of the disease, or both. Further, this information may be used for diagnosis of a plurality of medical conditions, such as glaucoma and age-related macular degeneration (AMD).

Combined Structure Function Analysis with RNFL Thickness and Direction Measurements In many ocular diseases, the structural and functional relationship on the retina is localized, meaning that a loss of function at a particular region of the retina may be attributed to some sort of a structural abnormality at the same location. For such diseases, the combined structural and functional evaluation may lead to evaluating the function of the retina at a plurality of points or regions and evaluating the structure of the retina at the same points or locations. The structural evaluation of the retina may be performed using an OCT device (e.g., OCT unit 202 of FIG. 2 or the structural evaluation unit 101 of FIG. 1) and may be used for evaluating a damage, detachment, blood flow, thinning of a specific retinal layer, or any other abnormality.

In the case of function loss due to neuropathy, such as glaucoma, the structural and functional relationships may be delocalized, meaning that the decrease in a function at one locality may be associated with a change in structure at a plurality of localities that may or may not include the locality of the decreased function. As an example, a decrease in sensitivity at a certain portion of the visual field may be associated with thinning of the RNFL at the peripapillary region of the optic nerve head. This delocalization is related to the anatomy of the ganglion cell axons and their arrangement in the RNFL. An attempt to map the spatial relationship between the locations on the retina and locations around the optic nerve head has been made by Harwerth et al. (R. S. Harwerth et al. "The relationship between nerve fiber layer and perimetry measurements" Invest Ophthalmol Vis Sci (2007) 48:763-773). FIGS. 3A-3D show a correspondence map developed between the visual field 301 and ONH sectors 302 using a non-human primate model.

Similar maps have shown good correlation between structure and function defects when applied to human glaucoma. See Garway-Heath et al., Beltagi et al., Reus et al., and Kerrigan-Baumrind et al. (D. F. Garway-Heath et al. "Mapping the visual field to the optic disc in normal tension glaucoma eyes" Ophthalmology (2000) 127:674-680,). (T. A. Beltagi et al. "Retinal nerve fiber layer thickness measured with optical coherence tomography is related to visual function in glaucomatous eyes" Ophthalmology (2003) 110: 2185-2191). (N. J. Reus et al. "The relationship between standard automated perimetry and GDx VCC measurements" Invest Ophthalmol Vis Sci (20 04) 45:840-845). (L. A. Kerrigan-Baumrind et al. "Number of Ganglion Cells in Glaucoma Eyes Compared with Threshold Visual Field Tests in the Same Persons" Invest Ophthalmol Vis Sci (2000) 41:741-748)).

For a more accurate visual field examination device with an increased accuracy of the stimulus location on the retina, maps that are generated using primate models or normative data may or may not perform adequately for accurate staging and progression analysis. Therefore, it may be beneficial to develop methods for determining individual RNFL fiber maps for patients undergoing screening and diagnostics for glaucoma using combined structure-function indices and analyses.

Several strategies for creating individual RNFL fiber direction maps are possible. Sugita et al. ("Retinal nerve fiber bundle tracing and analysis in human eye by polarization sensitive OCT" Biomed Opt Express. 2015 Feb. 26; 6(3):1030-54.) used polarization sensitive OCT (PS-OCT) to map the directions of retinal nerve fibers in the RNFL. In their assessment, the local retardation and fast axis measurements obtained with the PS-OCT were sufficient to determine the direction of the RNFL fibers around the optic disk and local variations in the RNFL thickness may be used to map the RNFL in it macular region. Sugita et al. demonstrated the ability of the PS-OCT system to map the direction of the RNFL fibers in the eye. Such information may be used to accurately trace individual RNFL fibers and develop correspondence maps between macula regions and RNFL in the peripapillary region. Such maps may be based on the actual measurement from the patient and may not necessarily depend on generalized correspondence maps or normative data.

Figure 4:
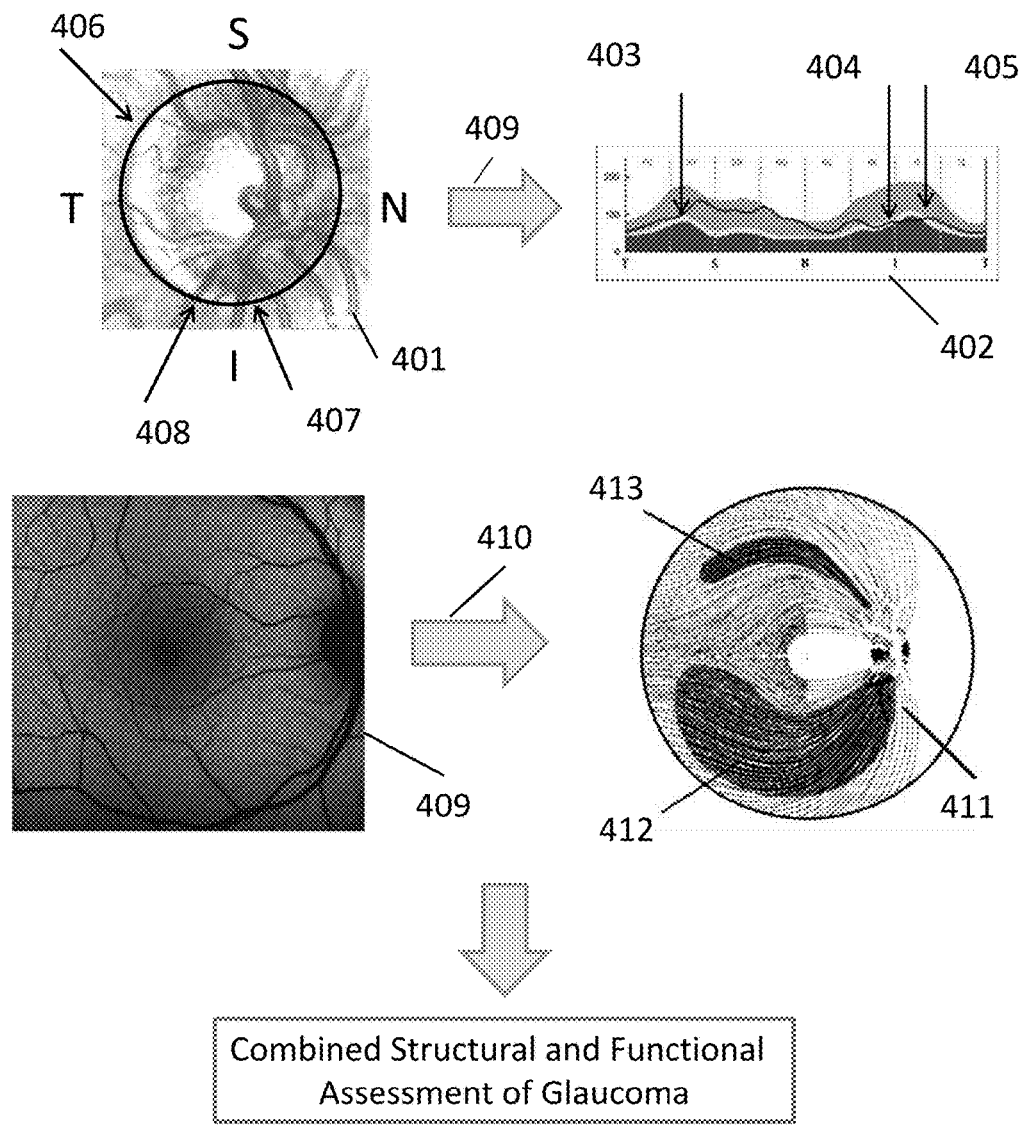
FIG. 4 is an illustration of an example process for obtaining a spatial relationship map for a retina, according to one or more embodiments.

FIG. 4 illustrates how spatial relationship maps may be obtained. Initially an OCT examination 401 may be performed around the ONH and a Temporal-Superior-Nasal-Inferior-Temporal (TSNIT) plot 402 of RNFL thickness may be generated 409. The RNFL thickness may be compared to a database (e.g., database 103 of FIG. 1) indicative of healthy, normal, or average RNFL thicknesses. Thus, regions of the peripapillary ONH that are associated with thinning of the RNFL 403, 404, and 405 (e.g., corresponding to 406, 407, and 408) may be identified.

A RNFL fiber orientation map 411 may be generated 410 using PS-OCT and locations of the abnormal RNFL thinning may be identified on the retinal image. Using the RNFL fiber orientation maps, regions 412, 413 of the retina that correspond to the abnormal thinning 412 in the peripapillary RNFL may be identified and the visual field function at the suspect regions may be evaluated. The visual field measurement may be later combined with the results of the structural examination in order to obtain a combined structure function evaluation and diagnosis. In this scenario, it is advantageous to use microperimetry, since the ability of precisely locating visual stimuli on the retina may allow for more accurate registration of the functional exam with the points on the retina affected by the RNFL thinning. Such accurate registration is likely to lead to more accurate diagnostics, progression evaluation, and follow up examinations.

Another approach to develop individual corresponding maps between various locations on the retina and the peripapillary region of the RNFL was demonstrated by Dennis et al. ("An anatomically customizable computational model relating the visual field to the optic nerve head in individual eyes" Invest Ophthalmol Vis Sci. 2012 Oct. 9; 53(11)). In Dennis et al., individual anatomical quantities such as axial length and relative position of the fovea and optic disk were combined with a mathematical model predicting the direction of the RNFL fiber growth. The model was used to predict the direction of the RNFL in the retina based on measurements taken directly from an individual patient and may be more accurate than normative data based models.

Both methods—direct RNFL fiber tracing using thickness variations combined with polarization sensitive methods and computational model predicting the RNFL direction based on measured anatomical properties may be used in the present disclosure in order to obtain individual RNFL maps and to provide a better correlation between a scotoma location and the RNFL thickness in the peripapillary RNFL (i.e., the region surrounding the optic nerve head). These methods may also be used to provide for planning perimetric examinations based on peripapillary RNFL thickness measurements as well as planning a structural examination based on functional examination.

In one or more embodiments, a combination of one or more measurements and mathematical models may be used to predict the individual RNFL maps. One example of such an implementation may include using OCT (e.g., the OCT unit 202 of FIG. 2) to evaluate the RNFL maps in the macula and peripheral retina region, where individual RNFL fiber bundles may be separately imaged and local variations in the OCT image may reveal the directions of the fiber propagation. The same implementation may utilize mathematical models with the actual subject's anatomical measurements as inputs in order to complete the mapping in the region where OCT may not be able to resolve individual fiber directions. Combining two such RNFL tracing algorithms, as illustrated in FIG. 5, may provide a reliable method of generating accurate individual RNFL maps for combined structural-functional evaluation of the retina.

Figure 5:
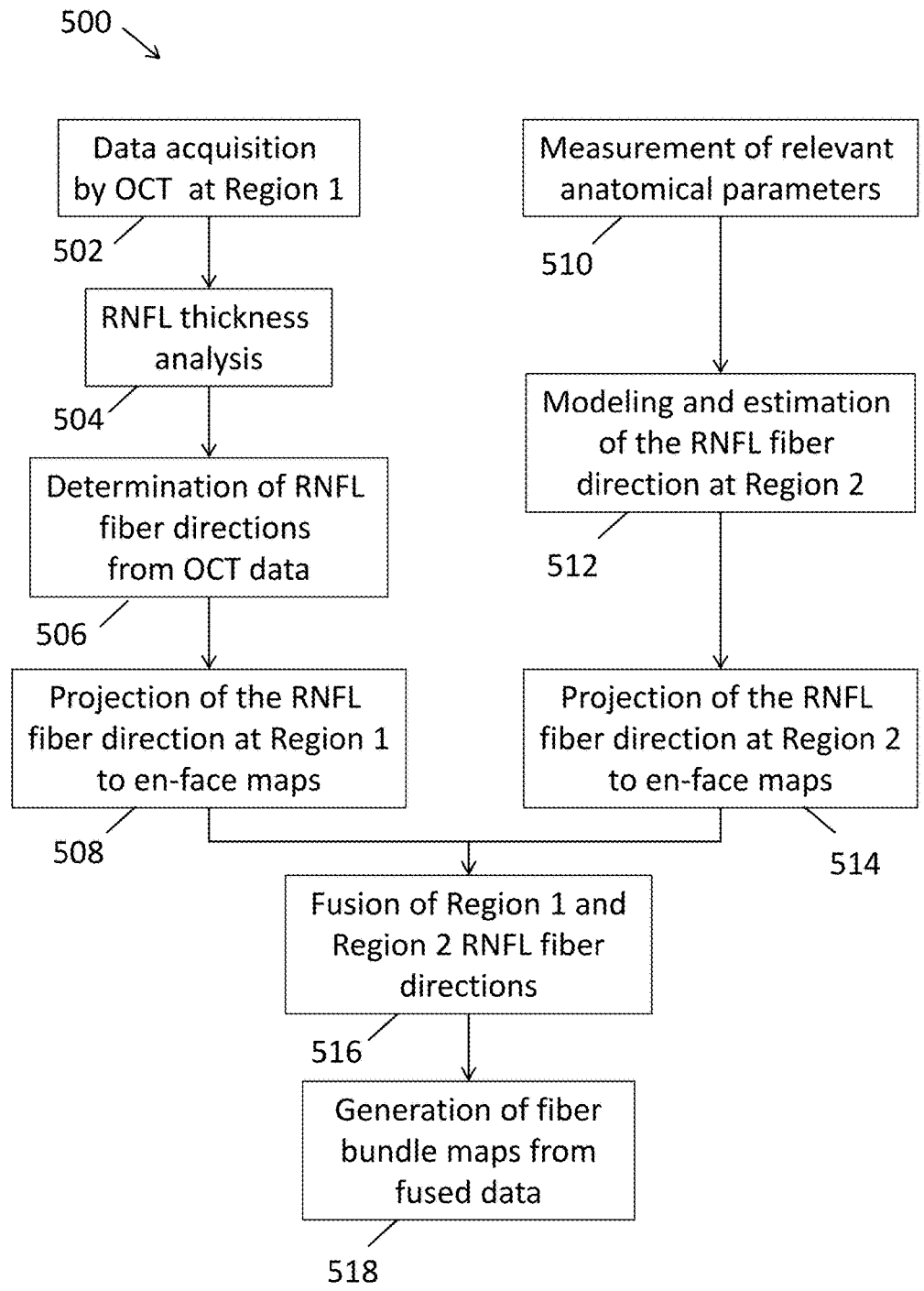
FIG. 5 is an illustration of an example flow diagram of a method for combined structural and functional evaluation of a retina, according to one or more embodiments.

FIG. 5 is an illustration of an example flow diagram of a method 500 for combined structural and functional evaluation of a retina, according to one or more embodiments. It will be appreciated that the methods, such as method 500 of FIG. 5 or 600 of FIG. 6, may be implemented using components, modules, or units of the systems 100 of FIG. 1, 200 of FIG. 2, 1400 of FIG. 14, or 1500 of FIG. 15. In this regard, data may be acquired by OCT at a first region at 502. RNFL thickness analysis may be conducted at 504 and determination of RNFL fiber directions based on OCT data may be performed at 506. At 508, the RNFL fiber direction of the retinal fibers at the first region may be projected to en-face maps. In one embodiments, 502, 504, 506, and 508 may be performed by the OCT unit 202 of FIG. 2 or the structural evaluation unit 101 of FIG. 1. At 510, anatomical parameters may be measured (e.g., at a second region). At 512, the RNFL fiber direction at the second region may be modeled and estimated. At 514, the RNFL fiber direction of the retinal fibers at the second region may be projected to en-face maps. At 516, data from the first region and the second region associated with the RNFL fiber directions may be fused. At 518, fiber bundle maps may be generated based on the fused data from 516.

According to one or more aspects, a combination of OCT in the macular region with PS-OCT may be utilized. According to other aspects, other types of RNFL fiber tracing may be used, such as PS-SLO and red-free imaging. It should be apparent to a person skilled in the art that any combination of different methods for RNFL measurement may be used in order to produce accurate individual RNFL maps.

Figure 6:
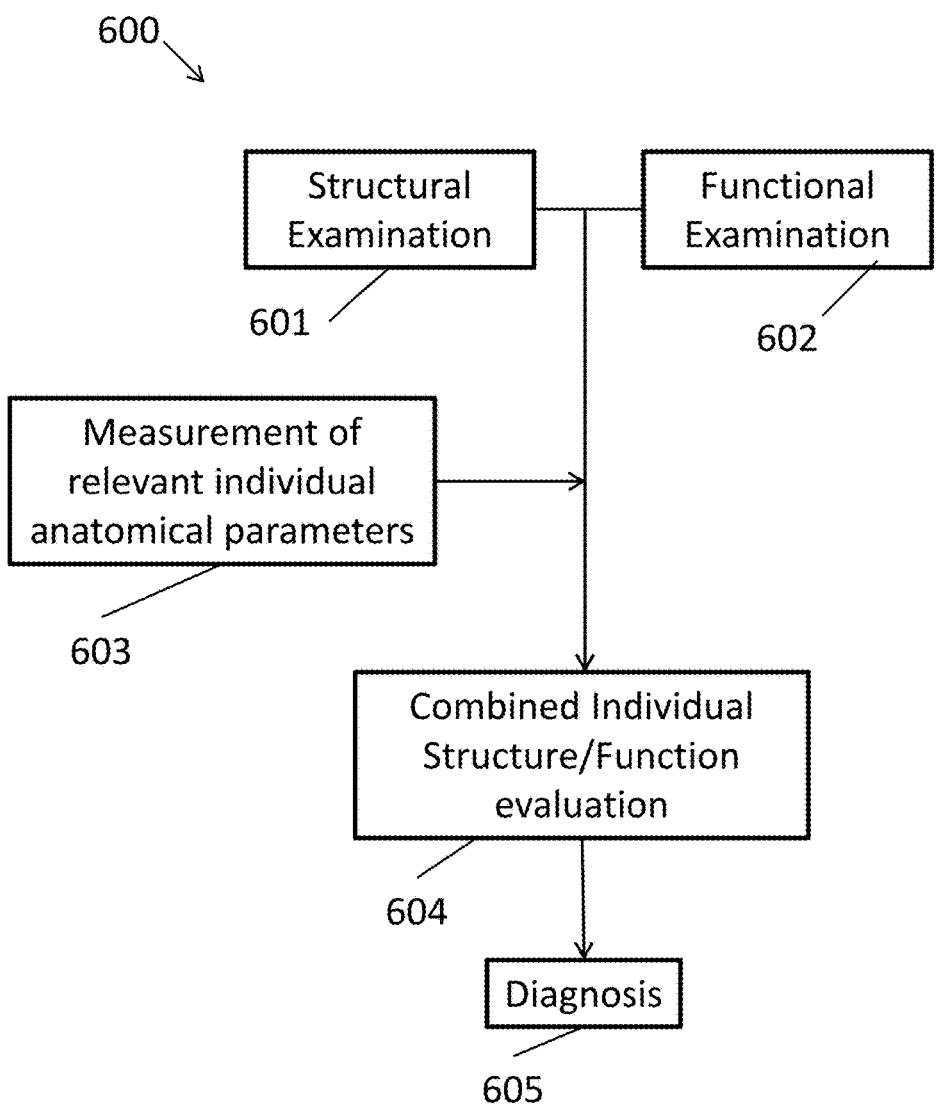
FIG. 6 is an illustration of an example flow diagram of a method for combined structural and functional evaluation of a retina, according to one or more embodiments.

FIG. 6 is an illustration of an example flow diagram of a method for combined structural and functional evaluation of a retina, according to one or more embodiments. Here, a combined structural examination 601 and functional examination 602 with an additional measurement of individual anatomical parameters 603 that provides a spatial correlation between the results obtained from structural and functional examinations 604 and a subsequent diagnosis 605. In this example, one measurement is performed that assesses the visual function of the subject, another measurement is performed that assesses the structure of the subject's retina, and the measurements are spatially correlated through a single or plurality of anatomical measurements that are specific to a subject.

In one or more embodiments, the anatomical measurements of 603 may be used to evaluate the direction of the RNFL fibers in the retina. These anatomical measurements may be OCT measurements (e.g., taken by the OCT unit 202 of FIG. 2 or the structural evaluation unit 101 of FIG. 1) of RNFL or other retinal layer thicknesses or a combination of measurement of the thicknesses of several layers. These measurements may be taken using red-free imaging with a scanning laser ophthalmoscope or a fundus camera. In other embodiments, these measurements may be PS-OCT measurements of the retardation, fast axis orientation of the RNFL layer, or both. As an example, an orientation angle of ganglion cell axons may be evaluated using red-free imaging, red-free SLO imaging, red-free adaptive optics SLO (AO-SLO) imaging, polarization sensitive SLO imaging, OCT thickness measurements, polarization sensitive OCT (PS-OCT) imaging, or any combination thereof. The orientation angle of ganglion cell axons may also be evaluated based on anatomical data not directly related to ganglion cells, such as blood vessel directions, axial length, location of the fovea, location of the optic disk, and the like. Other examples of anatomical measurements include axial length measurements of the eye, location of the fovea, location of the optic disk, or any combination of measurements.

In one or more embodiments, one or more of the anatomical measurements may be used to evaluate the direction of the RNFL fibers. Further, mathematical models or database information (e.g., from database 103 of FIG. 1) may be utilized to supplement the anatomical measurements in evaluating the RNFL fiber growth or the direction of the RNFL fibers.

Combining Visual Field with RNFL Thickness Measurements

Combination of the structural information about the retina with the functional information (e.g., measured by perimetry) in order to provide earlier and more accurate diagnostics for glaucoma as well as a more reliable modality for follow up has been studied. In some cases, it was found that the structural damage precedes measurable changes in the patient's visual field. For example, it was reported that as much as 30%-50% of ganglion cell loss would occur before changes in patient's vision could be measured with a perimeter. (H. A. Quigley et al. "Optic Nerve Damage in Human Glaucoma. III. Quantitative correlation of Nerve Fiber Loss and Visual Field Defect in Glaucoma, ischemic Optic Neuropathy, Papilledema, and Toxic Neuropathy" Arch Ophthalmol (1982) 100:135-146). (H. A. Quigley et al. "Retinal Ganglion Cell Atrophy Correlated with Automated Perimetry in Human Eyes with Glaucoma" AM J Ophthalmol (1989) 107:453-464). Thus, more emphasis may be placed on structural information in the early stages of glaucoma while using functional data for diagnostics and follow-up in more advanced stages of the disease. Hood et al. discloses the correspondence between structural and functional measurements, where both structural and functional measurements were represented in terms of ganglion cell axon counts in the peripapillary RNFL. (D. C. Hood, R. H. Kardon, "A framework for comparing structural and functional measures of glaucomatous damage" Progress in Retinal and Eye Research, Volume 26, Issue 6, November 2007, Pages 688-710). Thus, a direct comparison between the two values is possible.

Medeiros et al. discloses using a weighted average of the two values (i.e., the ganglion cell loss evaluated using mapping the RNFL thickness in a TSNIT map of the peripapillary region and the ganglion cell loss estimated from the mean deviation of the visual field). (F. A. Medeiros et al. "Estimating the rate of retinal ganglion cell loss in glaucoma" Am J Ophthalmol. 2012 November; 154(5):814-824). The weighted average of Medeiros et al. is depended on the MD index, is heavily shifted towards structural diagnostics for normal MD values, and gradually shifts towards heavier emphasis on the functional measurements in patients with lower MD index values.

In one or more embodiments, the combined individual structure/function evaluation at 604 may be performed by the structural evaluation unit 101 of FIG. 1. In other embodiments, the combined individual structure/function evaluation at 604 may be performed by the functional evaluation unit 102 of FIG. 1. Regardless, either unit 101 or 102 may be implemented with a processor and a memory, as will be described in FIGS. 14-15 herein. For example, the structural evaluation unit 101 may assign a combined structural and functional index based on computations other than weighted arithmetic averaging.

The structural evaluation unit 101 may assign a combined structural and functional index based on an arbitrary function (F). The arbitrary function (F) may be dependent on the structural index (si), functional index (fi), and mean deviation of the visual field (MD) that satisfies the following conditions:

F=si when MD approaches 0; and
F=fi when MD approaches a set constant value $MD_0$ of the mean deviation measured in dB.

$$F(si, fi, MD) = \begin{cases} si, MD \to 0 \\ fi, MD \to MD_0 \end{cases} \quad \text{(Eq. 1)}$$

$$F = [(x+y)/2] \text{ (Weighted Mean)} \quad \text{(Eq. 2)}$$

$$F = [(x^p + y^p)/2]^{1/p} \ (p \neq 1) \text{ (Weighted Power Mean)} \quad \text{(Eq. 3)}$$

$$F = [(x^p - y^p)/(p(x-y))]^{1/(p-1)} \quad \text{(Eq. 4)}$$
(Weighted Stolarsky Mean)

$$\sqrt{[(x^2 + xy + y^2)/3]} \text{ when } p = 3 \quad \text{(Eq. 5)}$$

$$F = (x^p + y^p)/(x^{p-1} + y^{p-1}) \text{ (Weighted Lehmer Mean)} \quad \text{(Eq. 6)}$$

$$F = [(x^p + y^p)/(x^r + y^r)]^{1/(p-r)} \quad \text{(Eq. 7)}$$

$$F = [(r(x^p - y^p))/(p(x^r - y^r))]^{1/(p-r)} \quad \text{(Eq. 8)}$$

$$F = [(x^p y^r + x^r y^p)/2]^{1/(p+r)} \quad \text{(Eq. 9)}$$

$$F = (x - y)/(\text{Ln}(x) - \text{Ln}(y)) \text{ (Weighted Log Mean)} \quad \text{(Eq. 10)}$$

$$F = (x\text{Ln}(x) + y\text{Ln}(y))/(\text{Ln}(x) + \text{Ln}(y)) \quad \text{(Eq. 11)}$$

$$F = (x + \sqrt{xy} + y)/3 \text{ (Weighted Heronian Mean)} \quad \text{(Eq. 12)}$$

$$F = (1/e)(x^x/y^y)^{1/(x-y)}, \quad \text{(Eq. 13)}$$
$e = 2.718281828 \ldots$ (Weighted Identric Mean)

$$F = (e)(x^y/y^x)^{1/(y-x)} \quad \text{(Eq. 14)}$$

$$F = (x^x y^y)^{1/(x+y)} \quad \text{(Eq. 15)}$$

$$F = (x^y y^x)^{1/(x+y)} \quad \text{(Eq. 16)}$$

In one or more embodiments, $MD_o=30$ dB. In other embodiments, the MD value may be calculated for the entire visual field or a subset of the entire visual field.

In one or more embodiments, F may be expressed in different forms of weighted averages. Exemplary implementations may include the following methods of calculating an average.

$$F=(x^y y^x)^{1/(x+y)} \quad \text{(Eq. 16)}$$

In other embodiments, F may be expressed as a weighted quadratic average:

$$F=\sqrt{[(x^2+y^2)/2]} \quad \text{(Eq. 17)}$$

Generally, x and y are represented by the following:

$x=si*(1-MD/MD_0)$; and $y=fi*(MD/MD_0)$

However, in some embodiments, weighted averaging is not utilized, and thus:

$x=si$; and $y=fi$

In yet other embodiments, the glaucoma index F may be computed as a linear or a nonlinear combination of the F-indices computed using Equations 2 through 17.

Further, in most of the equations, si and fi should be presented in the same units. In one or more embodiments, both structural measurements and functional measurements may be converted to a total ganglion cell axon count or a ganglion cell axon loss. In other embodiments, the structural index may be converted to a value representing a functional measurement or the functional index may be converted into a value representing a structural measurement. In this way, the structural evaluation unit 101 or the functional evaluation unit 102 may receive data and convert the data to a form which may be compared or evaluated in an 'apples to apples' manner because the data is converted to have the same units.

In other embodiments, a weighted mean may be calculated (e.g., using Eq. 9 by the structural evaluation unit 101) where si and fi are presented in different units. Using Eq. 9 for evaluating combined structural-functional index may be advantageous since there is no conversion of one type of measurement into another. As a result, the accuracy of the test result representation may improve. In such cases, the weighted averages for the structural and functional indexes may have specific scaling factors in order to provide accurate representation of the state of disease and progression.

Equations 2 through 17 are exemplary embodiments of the general Equation 1. In other embodiments, the function F may be scaled by multiplying F by a known constant. Doing so may simplify the index presentation by binding it in a convenient range for analysis. Examples of such ranges may be 0 to 1, 0 to 100, or other ranges that are conventionally used for describing an index or a severity of a given quantity.

In other embodiments, the glaucoma index F may be computed as a linear or nonlinear combination of the F-indices computed using any of the Equations selected from Equations 2 through 17.

Scotoma Edge Finding

Most glaucoma diagnostics and follow up are done using the 24-2 or 30-2 programs of the Humphrey perimeter. Both have a spatial resolution of 6-degrees, which arguably is not sufficient for detecting small changes in the visual field and for following progression of individual scotomas. (L. X. Chong at al. "Targeted spatial sampling using GOANNA improves detection of visual field progression" Ophthalmic Physiol Opt. 2015 March; 35(2):155-69). This spatial resolution limitation, combined with inability to track the retina may cause some variations in the follow up examination that are related to the test administration rather than to the actual progression of the disease.

Alternative solutions have been suggested. Haeberlin et al. discloses a procedure called the Spatially Adaptive Program (SAPRO), which tested locations at resolutions of 3.2-degrees, 1.6-degrees, and 0.8-degrees. (H Haeberlin and F. Fankhauser, "Adaptive programs for analysis of the visual field by automatic perimetry—basic problems and solutions. Efforts oriented towards the realisation of the generalised spatially adaptive Octopus program SAPRO" Doc Ophthalmol. 1980 Dec. 15; 50(1):123-41). While Haeberlin et al. improves the scotoma finding capability, the exam time is also significantly increased. Chong et al. discloses a gradient-oriented automated natural neighbor approach [GOANNA] that automatically chooses spatial test locations to improve characterization of visual field (VF) loss without increasing test times. (L. X. Chong at al. "Targeted spatial sampling using GOANNA improves detection of visual field progression" Ophthalmic Physiol Opt. 2015 March; 35(2): 155-69). Aoyama et al. discloses placing additional test points between the points of the 24-2 pattern in places where the visual field gradient is large order to better detect edges of scotomata. (Y. Aoyama et al. "A method to measure visual field sensitivity at the edges of glaucomatous scotomata" Invest Ophthalmol Vis Sci. 2014 Apr. 21; 55(4):2584-91).

In one or more embodiments, scotoma finding capabilities of the system 100 or 200 of FIG. 1 or 2 may be further advanced by utilizing the RNFL maps obtained from some of the measurements performed by the device or the systems 100 or 200. In the case of a glaucoma or other neuropathy diagnostics, it may be advantageous to not only map the visual field at a fixed set of locations on the retina, but also to characterize individual scotomas based on their size and mean deviation values. In such characterization, knowing the exact location of the edge of the scotoma may be advantageous for watching the progression of the disease.

In this regard, one may find that in some patients a mean deviation measured at a specific stimulus location of the 24-2 program may not change, but the scotoma may grow larger in size. In such cases, the disease will appear to be stable until the scotoma reaches another stimulus point in the 24-2. It is well known that 24-2 presents more stimulus points for some sectors of the peripapillary RNFL and less for other sectors. In the peripheral retina, where a sector of RNFL may have only 2 or 3 corresponding presentations in the 24-2, a scotoma growth may not be recognized and the disease progression may be underestimated. Thus, it may be advantageous to find the exact edges of the scotoma in order to have a meaningful follow up examination.

In one or more embodiments, systems and methods for combined structure and function evaluation of retina may include detecting and displaying one or more edges or boundaries of one or more scotomatous damages in the eye and showing the progression of these edges or boundaries due to the disease progression or treatment, such as via the structural evaluation unit 101 or the functional evaluation unit 102 of FIG. 1. Scotoma boundaries may be defined as a region of the scotoma where the visual field transitions from one certain value to another (isopters), defined as regions of the scotoma that have a certain deviation from a normal region, or defined in any way that separates a region of damage from a normal region of the visual field. The normal values may be calculated based on the specific measurements for a given patient or may be determined from a normative database (e.g., database 130 of FIG. 1).

In one or more embodiments, the scotoma edges may be found by adjusting the stimulus presentation locations during the visual field examination based on the previous responses and RNFL maps. A search for scotoma boundaries may be conducted in directions perpendicular to the alignment directions of the RNFL fibers. Since glaucomatous damage tend to propagate along the direction of the fiber bundles, a search algorithm that looks for the scotoma edges in the direction perpendicular to the RNFL fibers may be quicker in finding scotoma boundaries than other methods, as outlined in FIG. 7.

Figure 7:
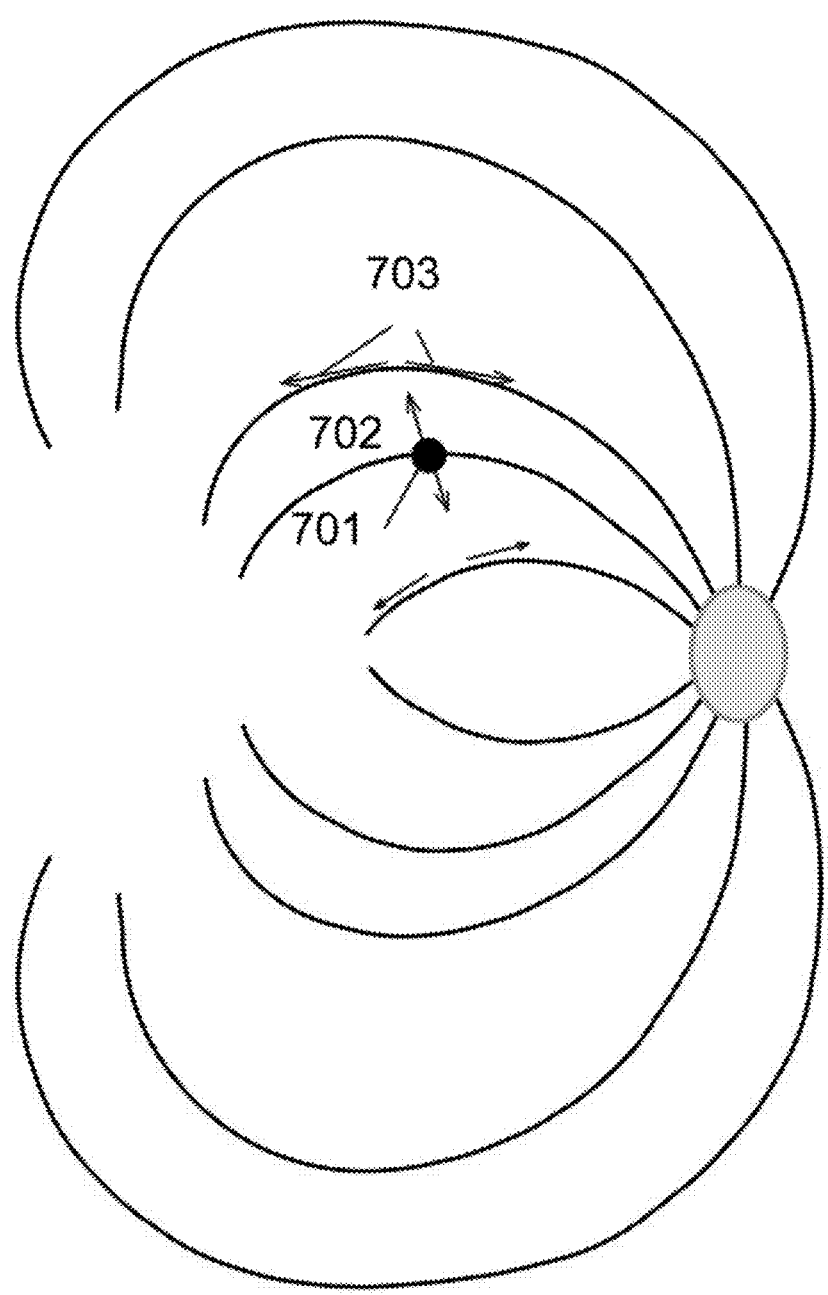
FIG. 7 is an illustration of example RNFL fibers in relation to scotoma edge finding, according to one or more embodiments.

FIG. 7 is an illustration of example RNFL fibers in relation to scotoma edge finding, according to one or more embodiments. In this regard, once a single defect point 701 in the visual field is detected, a search for a scotoma boundary continues perpendicular 702 to the RNFL fiber propagation with the starting point at the detected visual field defect. In other words, when the edges of the scotoma are found, as defined by a pre-determined algorithm, the stimuli are presented along the RNFL fiber bundles. If the presented stimulus meets the criteria for scotoma boundary, the next stimulus presentation is moved along the fiber direction 703. If the stimulus doesn't meet the scotoma boundary criteria, the following stimulus is moved perpendicularly 702 to the RNFL fibers until a boundary is found.

The initial points of the scotoma may be found using OCT scan of the peripapillary RNFL and subsequent identification of candidate points based on the RNFL thinning. Alternatively, a subset of 24-2 points may be used in such manner that at least a certain number of points are mapped per sector of a TSNIT scan. It may be advantageous to use test programs developed by Asaoka et al., which discloses a new point distribution called DCF. (R. Asaoka et al. "A novel distribution of visual field test points to improve the correlation between structure-function measurements" Invest Ophthalmol Vis Sci. 2012 Dec. 19; 53(13):8396-404).

In one or more embodiments, a visual field testing method may be derived from adaptive sparse grid interpolation techniques for interpolating multi-dimensional functions. These techniques were developed for quick interpolation of a function with a smallest number of measurement points. The idea behind this is to iteratively decide where to place the next measurement point based on the prior measurements rather than using a pre-determined grid. In other words, the location of the points are not selected from a pre-determined grid, but may be derived during the course of examination as a function of the patient's previous responses.

Presentation of Combined Structure-Function Test Results

[NFL+GCL+IPL] and NFL thickness may be early biomarkers for structural damage due to glaucoma. Thus, OCT guided perimetry may be a useful tool for more accurate assessment of visual field loss in early glaucoma patients. A number of embodiments of glaucoma diagnosis may thus be developed which utilize the structure properties obtained with OCT or other eye fundus imaging techniques, combined with function information obtained using visual field examination with a perimeter.

In one or more embodiments, the OCT data (e.g., gathered by the structural evaluation unit 101 of FIG. 1 or the OCT unit 202 of FIG. 2) may be spatially registered with the visual field examination data and the visual field may presented on a screen (e.g., by the functional evaluation unit 102 of FIG. 1, the display 201 of FIG. 2, or other display which is not necessarily the display 201) for evaluation and the thickness of the retina nerve fiber layer at a single location (or plurality of locations selected by the examiner) may be presented on the screen for examination. For example, the value of the NFL thickness of a point may be displayed by hovering a cursor over a certain area on the visual field, or by displaying the visual threshold value at a point on the fundus image by hovering the surface over the image.

In other embodiments, the OCT data may be spatially registered with the visual field examination data and the visual field may be presented on the display of a computing device (e.g., output device 1522 of FIG. 15) for evaluation, and the examiner may select a line or a plurality of lines passing over the visual field. In these embodiments, the thickness of the retina nerve fiber layer or the ganglion cell complex may be displayed in a form of a graph or plurality of graphs on the display. For example, by selecting two points on the visual field or the fundus image and drawing a line connecting the two points, graphs of the visual field and a relevant parameter such as NFL or [NFL+GCL+IPL] thickness obtained from an OCT data may be displayed.

In yet another embodiment, damage to the optic nerve may be assessed using an OCT image of the optic disk and the visual field examination may be performed at a set of examination points predetermined based on the knowledge of anatomy and OCT image of the optic disk. In other words, the structural evaluation unit 101 may record the OCT image of the optic disk and the functional evaluation unit 102 may perform the visual field examination at a set of examination points based on the OCT image or information from the database 103.

In one or more embodiments, glaucoma diagnostics may be provided by measuring the retina nerve fiber layer using the structural evaluation unit 101 and the visual field may be measured using a visual field examination device, such as the functional evaluation unit 102 of FIG. 1. These two measurements may be spatially registered and a cross-correlation or localized weighted average function may be calculated (e.g., by either unit 101 or 102 or the processor 1516 or memory 1518 of FIG. 15) between the two fields. The resulting data may be presented on a computer screen (e.g., output device 1522 of FIG. 15) representing a color or grey scale coded OCT map of the RNFL, a color or grey scale coded OCT map of the visual field, or a color or grey scale coded OCT map of the correlation function.

In one or more embodiments, combined information about the structural examination may be compared to the visual function measured by a visual field examination device in order to assess the state of disease and its rate of progression. In one or more embodiments, the spatial correspondence maps of the RNFL in the peripapillary region and various locations on the retina may be combined with the visual field examination in order to provide a tool for diagnostics, screening, examination, and follow up assessment for neuropathy related conditions such as glaucoma.

Different variations may be implemented where the combined structure-function index may be computed for the entire visual field of an eye or for a specified region or plurality of specified regions contained within the visual field of the eye. Similarly, the boundary of scotomatous damage may be computed for the entire visual field of the eye or for individual scotomas or combined with the visual field index in the scotoma to compute the index corresponding to the severity of individual scotoma. The combined structure-function index may be computed for a plurality of points contained within the visual field of the eye or presented to the examiner for evaluation, diagnostics, or follow up.

Combined structure-function indexes may be computed for one or more specified regions and presented to the examiner for evaluation and diagnostics. In one or more embodiments, a map of combined structure-function index computed for a plurality of points may be presented to the examiner for evaluation and diagnostics. This map may include a visual field index map or be overlaid over the fundus image or SLO image of the retina. The boundary of scotomatous damage for the entire visual field of the eye or for individual scotomas may be presented to the examiner for evaluation and diagnostics. In other embodiments, the boundary of scotomatous damage combined with the visual field index in the scotoma to compute the index corresponding to the severity of individual scotoma may be presented to the examiner for evaluation and diagnostics.

Customizing Visual Field Exam Based on RNFL Thickness Measurements

Quick visual field examination is a desirable feature for any perimeter. Many perimeters require continuous attention from the patient for several minutes. For some patients, it is difficult to keep the same position for such a long time, because patients move, lose fixation, stop paying attention to the stimuli, and the like. This results in prolonged examination, and subsequently erroneous test results. Very rarely is a perimetry examination included in a patient screening, and this is mainly due to the length of time it requires to conduct an exam.

One method for accelerating perimetric examination is by limiting or reducing the number of stimuli presentation points. However, in conventional perimetry, this may result in missing glaucomatous damage. In the combined structure-function based examination disclosed herein, the probability of missing glaucomatous scotoma may be reduced if a structural examination is performed first and the functional examination is performed at the points that are suspected to have reduced visual field based on the structural examination results.

In one or more embodiments, the thickness of the [NFL+GCL+IPL] may be mapped over the macula and areas with reduced [NFL+GCL+IPL] layer thickness may be identified (e.g., by the structural evaluation unit 101 or functional evaluation unit 102 of FIG. 1). Several visual stimuli may be presented in the area of the thin [NFL+GCL+IPL] and several stimuli may be presented at the area with normal [NFL+GCL+IPL] thickness. If any reduction in the visual field is found, then a complete functional examination of the visual field may be conducted.

In other embodiments, the RNFL thickness may be measured in the peripapillary region of the optic nerve head and areas with reduced RNFL layer thickness may be identified. A correspondence map between the peripapillary region and the retina may be mapped and areas on the retina corresponding to a suspected damage in the RNFL may be identified. Several visual stimuli may be presented in the area of the suspected scotomas and several stimuli may be presented at the area with suspected normal visual field. If any reduction in the visual field is found, then a complete functional examination of the visual field may be conducted.

In one or more embodiments, the birefringence of the RNFL thickness may be measured in the peripapillary region of the optic nerve head and areas with reduced RNFL layer birefringence may be identified. A correspondence map between the peripapillary region and the retina may be mapped and areas on the retina corresponding to a suspected damage in the RNFL may be identified. Several visual stimuli may be presented in the area of the suspected scotomas and several stimuli may be presented at the area with suspected normal visual field. If any reduction in the visual field is found, then a complete functional examination of the visual field may be conducted.

Selecting Structural Evaluation Measurement Based on Visual Examination

In one or more embodiments, spatial correspondence maps of the RNFL in the peripapillary region and various locations on the retina may be used to select regions for structural evaluation of the retina based on the outcomes of the functional evaluation. In such embodiments the structural examination may be performed at the location of the abnormal visual field examination (e.g. [NFL+GCL+IPL] thickness measurements at the macula) or at a different location of the retina. In other words, the structural evaluation unit 101 may select and evaluate regions of the retina based on the outcomes of the functional evaluation performed by the functional evaluation unit 102 or spatial correspondence maps of the RNFL in the peripapillary region. Here, the functional evaluation unit 102 may perform a visual field examination and a specific structural exam on a part of the retina may be conducted (e.g., by the structural evaluation unit 101) based on the results of the visual field examination. The examination may be an en-face OCT examination, a higher resolution than normal OCT exam, a TSNIT OCT map exam, an OCT B-scan oriented in a specific direction, or the like.

Conversely, the functional evaluation unit 102 may perform different visual field examination depending on or based on the results of the structural examination performed by the structural evaluation unit 101.

Tracking and Fixation Improvements

Figure 8:
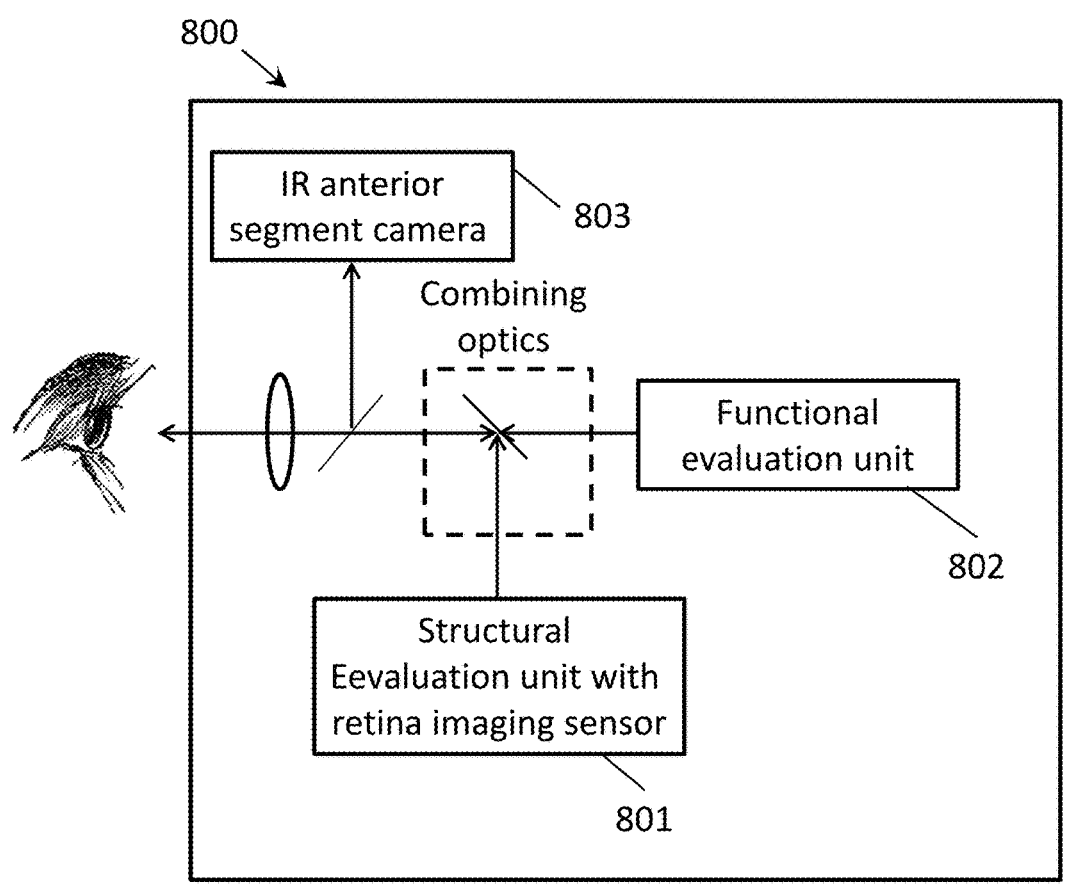
FIG. 8 is an illustration of an example gaze tracking system for combined structural and functional evaluation of a retina, according to one or more embodiments.

FIG. 8 is an illustration of an example gaze tracking system 10 for combined structural and functional evaluation of a retina, according to one or more embodiments. The system 10 may image and track the retina of the patient in real time and register the exact location of the visual stimulus on the retina, thereby providing accurate and robust eye tracking and enabling other components, such as the structural evaluation unit 101 or the processor 1516 to generate accurate correspondence maps based on the structural and functional evaluations.

The gaze tracking system 10 may include an imaging sensor (e.g., IR anterior segment camera 32) that uses the image of the anterior segment of the eye 17 in order to determine the gaze direction. The imaging sensor may be connected to a computing device (e.g., system 1500 or computing device 1512 of FIG. 15) that analyzes one or more features of the eye, such as the limbus, pupil, blood vessels, or other features visible in the eye image. In other embodiments, multiple (e.g., two or more) imaging sensors may be configured to image the anterior surface of the eye in order to obtain the gaze direction from a stereoscopic view of the eye surface. Regardless, the imaging sensor may be configured to image the retina and register the location of the visual stimulus to an associated location on the retina.

The gaze tracking system 10 may include a light source (e.g., IR source 11) configured to produce a glint on the surface of the cornea and a relative location of the glint to a visible feature of the eye to determine the gaze direction. According to other aspects, two or more imaging sensors may be combined with one or more light sources to produce one or more glints on the surface of the cornea. The gaze tracking system 10 may also include a torsional tracking system (not shown) to further increase the accuracy of locating the visual stimulus.

In one or more embodiments, a pressure sensor (not shown) or a touch sensor (not shown) may be employed, such as on the forehead rest or chin rest of the gaze tracking system 10, system 100, or system 200 in order to detect a change in the patient's position and provide a warning to the computing device (e.g., system 1500 or computing device 1512 of FIG. 15) that the patient's head position has changed. In this way, the computing device 1512 may take corrective action, such as by adjusting a location of a visual stimulus to be presented by the functional evaluation unit 102, etc.

In the embodiment depicted in FIG. 8, a combination of two or more imaging sensors may be used to simultaneously or subsequently image the anterior surface of the eye and the retina. Here, a first imaging sensor configured to image the retina may be part of the structural evaluation unit 801 and second imaging sensor or IR anterior segment camera 803 may be configured to image the anterior surface of the eye. The system 800 may use the retina image for calibration and alignment checking, while the anterior surface image may be used when the quality of the retina image is insufficient for locating the stimulus and gaze direction tracking.

In perimetry, the gaze direction determination plays a passive role and may be used to reject a data point or plurality of data points when the gaze direction deviated from a fixation target. However, patients with poor fixation would be subject to a longer examination. To address this, the functional evaluation unit 102 of FIG. 1 or the perimeter may adjust a location of a visual stimulus based on the direction of the gaze or associated information. In this way, visual stimuli may be presented on a desired location on the retina and the visual field examination will take less time due to the absence of dropped data points.

Figure 9:
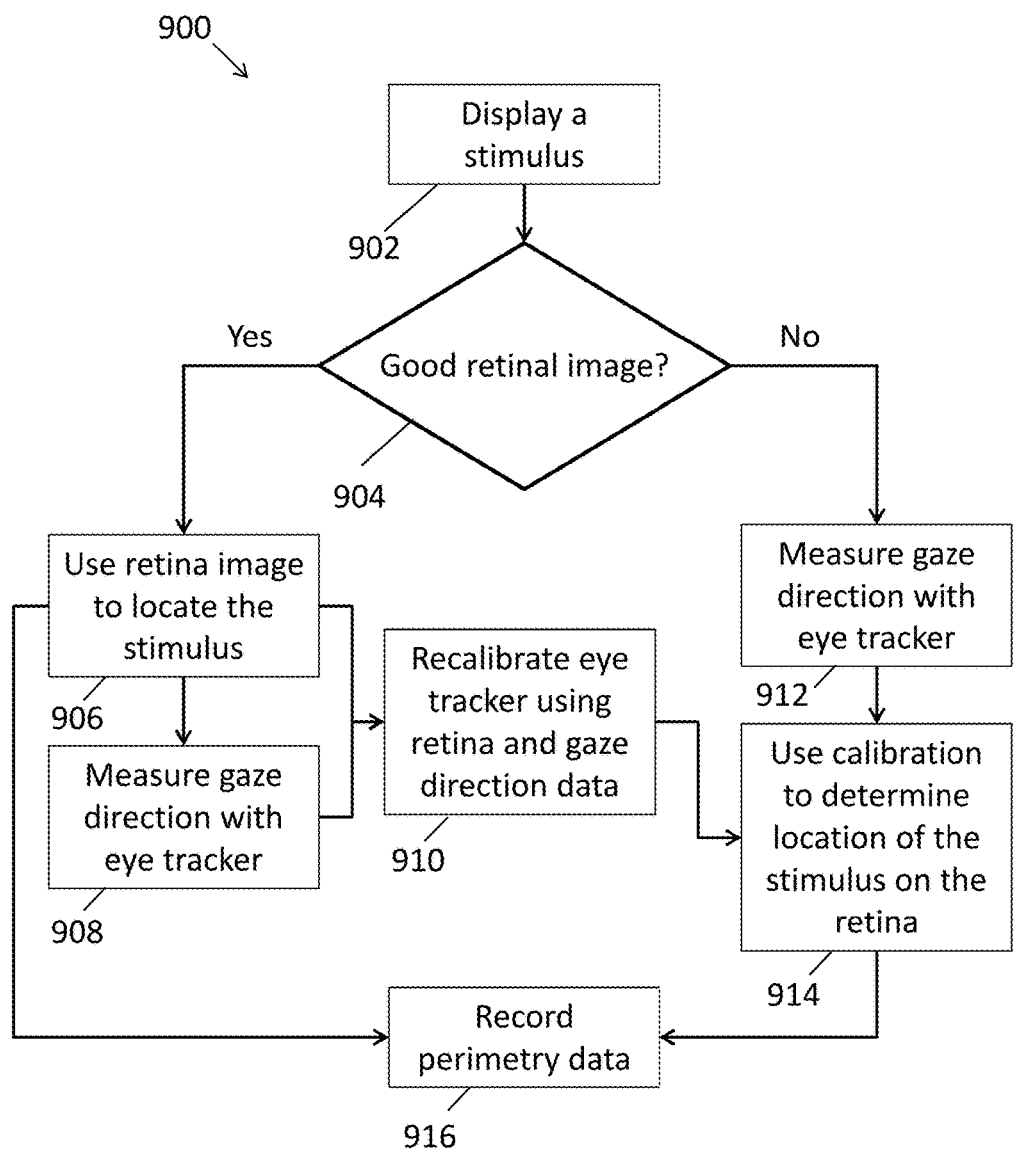
FIG. 9 is an illustration of an example flow diagram of gaze tracking in relation to a method for combined structural and functional evaluation of a retina, according to one or more embodiments.

FIG. 9 is an illustration of an example flow diagram of gaze tracking in relation to a method 900 for combined structural and functional evaluation of a retina, according to one or more embodiments. The method 900 may include displaying a stimulus 902 at a location, determining whether a retinal image is good (e.g., no cataract) at 904, using the retina image to locate the stimulus 906 if the retinal image is good, and measuring gaze direction with an eye tracker 908. At 910, the eye tracker is recalibrated using retina and gaze direction data. If the retinal image of 904 is not good, the gaze direction is measured with the eye tracker at 912. At 914, the location of the stimulus on the retina is determined using calibration and perimetry data is recorded at 916.

In one or more embodiments, the functional evaluation unit 102 or optical system 10 (e.g., on display 29) for presenting the visual stimulus may be configured to simultaneously present a dim visual stimulus in a visible wavelength and a spatially coregistered bright stimulus in the IR wavelength invisible to the subject's eye. Thus, the location on the retina illuminated by the IR light (e.g., IR source 11) may be imaged using an IR imaging sensor 23. Since the two lights are coregistered the location of the visible stimulus will likely be the same as the location of the IR spot on the retina.

In many cases, a severe or even mild cataract may impede the ability to image the retina of the subject's eye and may make the visual field exam using retina based eye tracking impractical. In such cases, it is advantageous to utilize image processing methods that will allow reconstructing the features of the retina imaged through the cataract.

Figure 10:
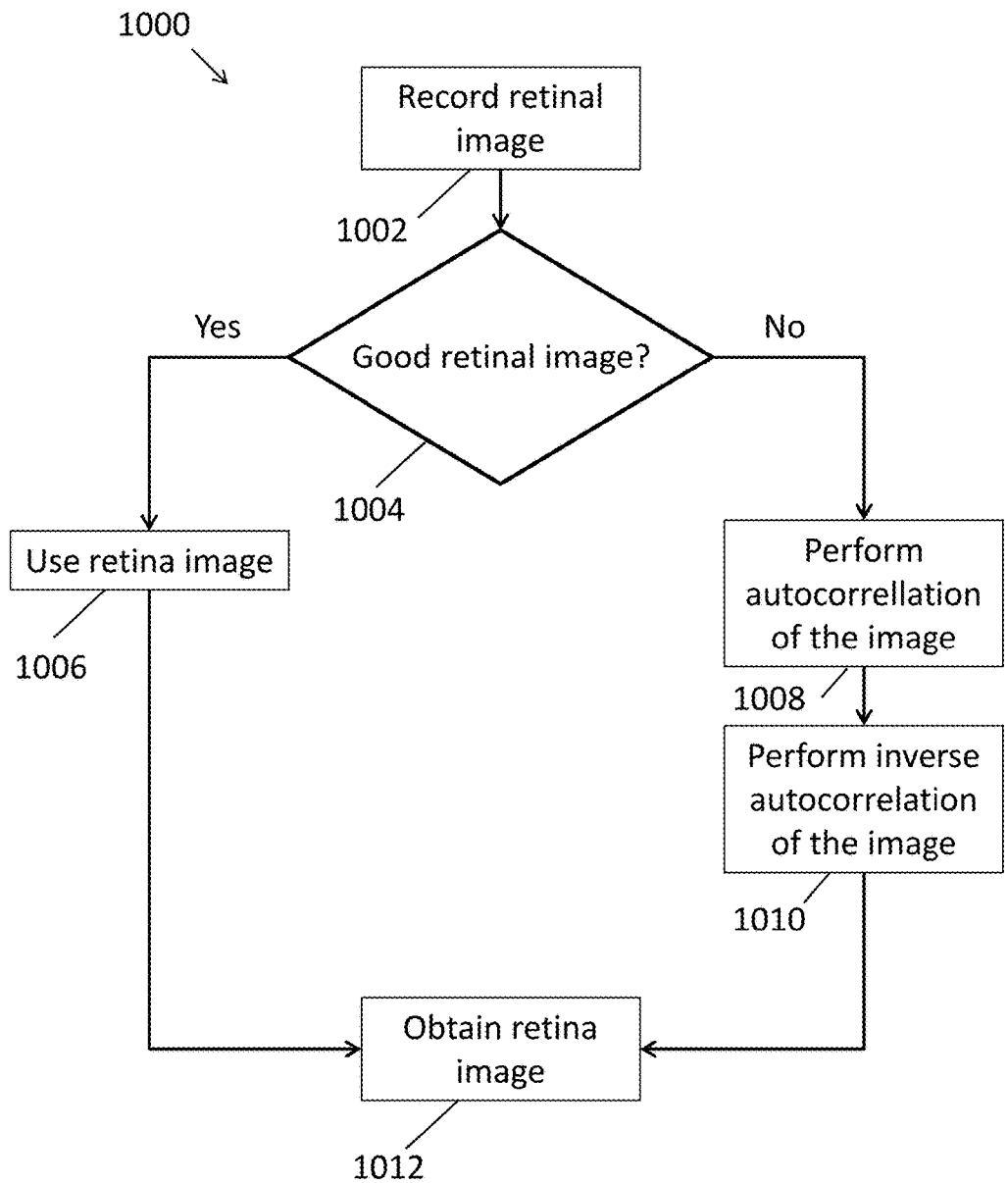
FIG. 10 is an illustration of an example flow diagram of image selection in relation to a method for combined structural and functional evaluation of a retina, according to one or more embodiments.

FIG. 10 is an illustration of an example flow diagram of image selection in relation to a method 1000 for combined structural and functional evaluation of a retina, according to one or more embodiments. The method 1000 may include recording an image of the retina through a cataract 1002, determining whether the retinal image is good 1004, and using the retina image if good 1006 (e.g., no cataract). If the image of 1004 is not found to be good, the method 1000 may include calculating the autocorrelation function of the image 1008, and using an iterative phase retrieval or other inverse algorithms 1010 to obtain the original image 1012. In this way, the retina image of 1012 is produced in a manner which includes a more usable image of the retina than the retinal image of 1002, imaged through the cataract.

During a visual field examination, one eye of the subject may be covered, while the other eye is directed towards a fixation target. However, when subjects have poor vision or cannot maintain a stable fixation on the target, the exam time may increase due to a larger number of rejected data points. In this regard, the system 10 or 100 may provide the visual stimulus to merely one eye while allowing the subject to use both eyes for fixation.

For example, the system 10 may be configured such that a first eye of the patient is directed into the instrument that is performing a visual field examination (e.g., functional evaluation unit 102 of FIG. 1) and a second eye of the patient is directed towards a gaze fixation target including the illumination source 11 and an optional lens 16 positioned in front of the eye 17. Further, the position of the gaze fixation target in the second eye may be spatially tied to the gaze fixation target in the first eye.

In one or more embodiments, the fixation target for the second eye may be positioned on a movable, rotating, or swinging mount such that it may be moved to the right or the left eye of the patient, while the examination is performed on the other or first eye.

Probability Based Progression Evaluation

In perimetry, the visual field data is presented in a format where a threshold value in dB is presented as a function of location in the visual in x- and y-angular coordinates. This may be described as $I_t=f(x,y)$, where It is the threshold intensity and x, y are the angular coordinates. However, for patients with severe visual field damage it may be more accurate to present the data as the probability of detection of the visual stimulus (P) as a function of stimulus intensity, and its angular coordinates. (S. K. Gardiner et al. "Effect of response saturation on the test-retest correlation in damaged visual fields" Sep. 9-12, 2014 21st International Visual Field and Imaging Symposium 2014 New York City, N.Y.). This representation may be described as $P=f(I,x,y)$, where P is the probability of detection and I is the intensity of the stimulus. The solution of the equation $0.95=f(It,x,y)$ represents the result of perimetry.

In one or more embodiments, the probability of detection may be plotted on the display of the computing device 1512 for better representation of the disease state. In other embodiments, the measurement of detection probabilities as a function of stimulus intensity may be used for determination of the progression of the visual field change.

Additional Exemplary Embodiments

Figure 11:
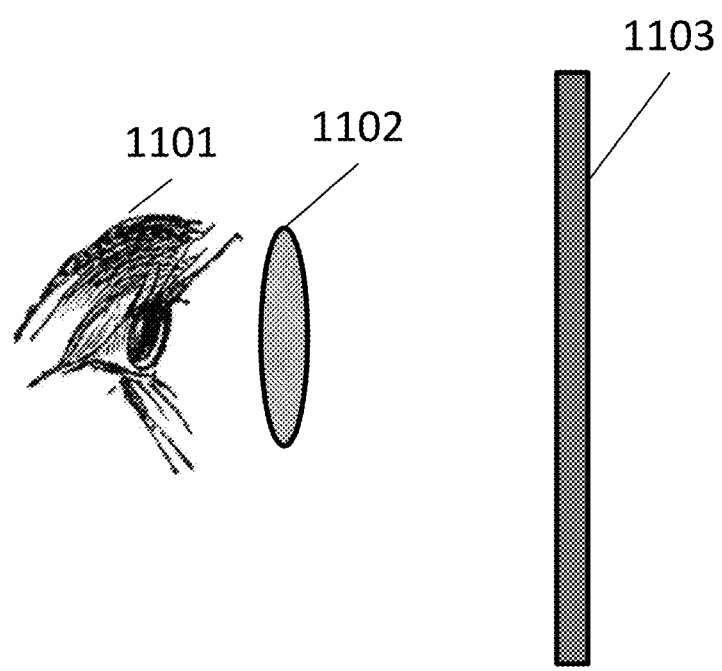
FIG. 11 is an illustration of an example implementation of a system for combined structural and functional evaluation of a retina, according to one or more embodiments.

In one or more embodiments, illustrated in FIG. 11, a perimeter (e.g., functional evaluation unit 102) may include a display 1103 connected to a computing device (e.g., 1512 of FIG. 15) such that visual stimuli may be presented directly on the display 1103. A specialized optics 1102 may be placed between the subject's eye 1101 and the display screen 1103. The specialized optics 1102 may have active and passive optical components and may be used to control the focal distance, perceived brightness, and field of view of the subject's eye 1101. The fixation target may be presented directly on the display 1103 and its position may be changed to control the subject's gaze direction.

Figure 12:
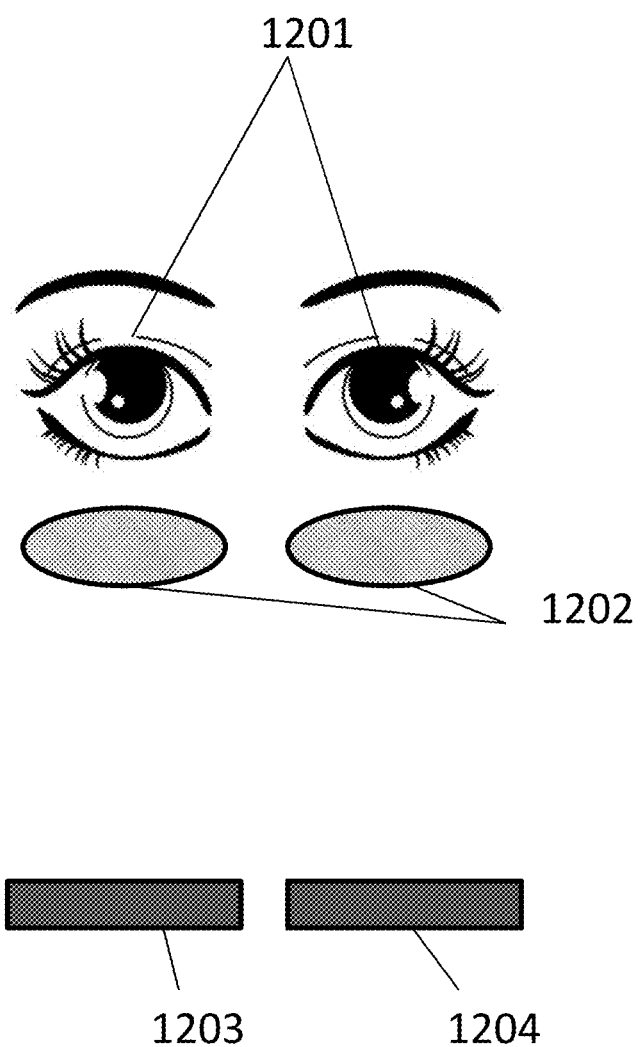
FIG. 12 is an illustration of an example implementation of a system for combined structural and functional evaluation of a retina, according to one or more embodiments.

In another embodiment, illustrated in FIG. 12, the perimeter may include two displays 1203, 1204 connected to a computing device (e.g., 1512 of FIG. 15), such that one eye 1201 of the subject is looking at one display 1203 while the other eye 1201 of the subject is looking at another display 1204.

Figure 13:
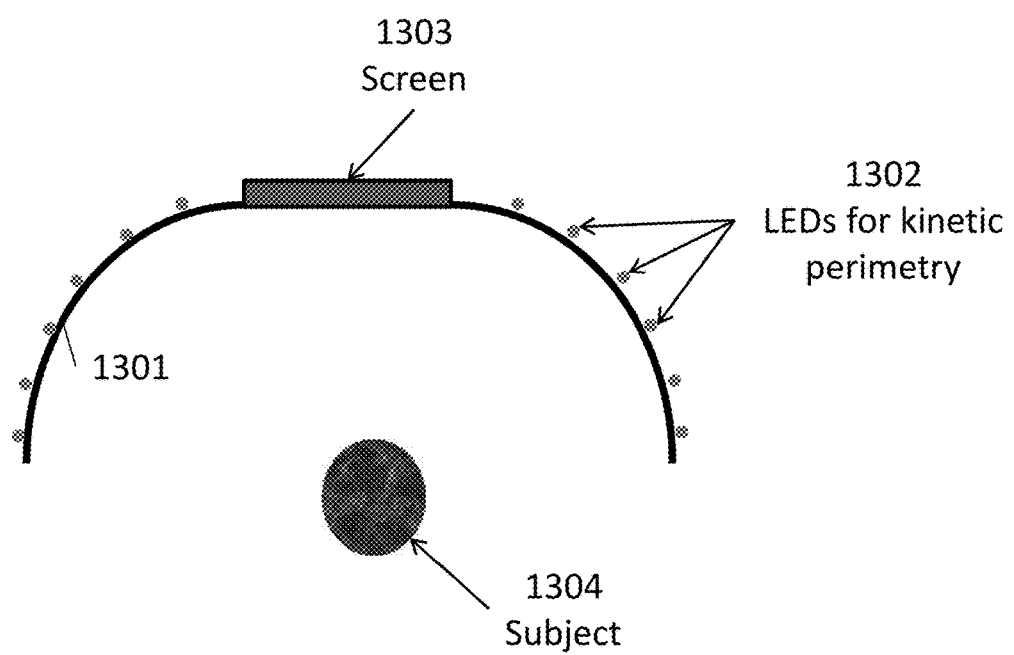
FIG. 13 is an illustration of an example implementation of a system for combined structural and functional evaluation of a retina, according to one or more embodiments.

To increase the angle of the tested visual field, it may be advantageous to combine one or more of the embodiments described herein with a dome shaped object 1301 such that visual stimuli may be presented on the inner surface of the object, as depicted in FIG. 13. As an example, the surface of the object 1301 may have diffuse reflective characteristics and the visual stimuli may be projected on its surface using a projector, or the inner surface of the object may be made of transparent or scattering material and the visual stimuli may be presented using LEDs 1302 or other light sources positioned behind the inner surface of the dome shaped object 1301. In this manner, the stimuli may be viewable by the subject 1304 on the dome shaped object 1301 or screen 1303.

It will be appreciated that the visual stimuli may have various colors or varying intensities while also having a background of various colors and intensities. For example, the intensity of the presented visual stimulus may be lower than the intensity of the background on which it is presented. The display or screen 1303 may be used to present an alternating set of dark and bright lines changing their brightness as a function of time in order to perform a frequency doubling perimetry examination.

DEFINITIONS

AMD—age-related macular degeneration
AO-SLO—adaptive optics scanning laser ophthalmoscope
DCF—disk-centered field
DMD—digital micromirror device
[NFL+GCL+IPL] nerve fiber layer+ganglion cell layer+ the inner plexiform layer
GOANNA—gradient-oriented automated natural neighbor approach
HFA—Humphrey field analyzer
IR—infrared
LCD—liquid crystal display
LCoS—liquid crystal on silicon
LED—light emitting diode
MD—mean deviation
NFL—nerve fiber layer
OCT—optical coherence tomography
Patient—may be used interchangeably with 'subject'
PS-OCT—polarization sensitive optical coherence tomography
PS-SLO—polarization sensitive scanning laser ophthalmoscope
RNFL—retinal nerve fiber layer
SAPRO—Spatially Adaptive Program
SITA—Swedish interactive thresholding algorithm
SLO—scanning laser ophthalmoscope
SWAP—short wave automated perimetry
VF—visual field In some aspects of the disclosure, the visual examination may be done separately and independently from the structural examination of the eye.

In a 1st aspect, a perimeter includes a LCD, LED, or plasma display and specialized viewing optics positioned between the display and the subject's eye.

In a 2nd aspect, a perimeter includes a LCD, LED, or plasma display and specialized viewing optics positioned between the display and both eyes of the subject, wherein the viewing optics is configured such that the stimulus may be presented only to one, or the other, or both eyes of the subject at a time.

In a 3rd aspect, a perimeter includes a LCD, LED, or plasma display surrounded by a dome shaped screen wherein visual stimuli may be presented both on the display and on the dome shaped screen.

In a 4th aspect, a perimeter includes a LCD, LED, or plasma display surrounded by a dome shaped object outfitted with a plurality of LEDs or similar miniature light sources, wherein visual stimuli may be presented both on the display or on the dome shaped object using the slight sources.

In a 5th aspect, a perimeter includes two LCD, LED, or plasma displays and specialized viewing optics positioned between the display and eyes of the subject, wherein the viewing optics is configured so that one eye of the subject is looking at one display and another eye of the subject is looking at another display.

In a 6th aspect, a system of any aspects 1-5 includes an eye gaze direction tracking system.

In a 7th aspect, a system of any aspects 1-5 includes a capability of performing one or more of SWAP and frequency doubling visual field measurements.

In an 8th aspect, a perimeter wherein the fixation target may be simultaneously presented to both eyes, while the visual stimulus may be presented to one eye or the other.

In a 9th aspect, a perimeter includes a visual stimulus presentation system and an eye gaze tracking system, wherein the eye gaze tracking system is capable of obtaining images from the anterior segment of the eye and the retina.

In a 10th aspect, a perimeter includes a visual stimulus presentation system and an eye gaze tracking system, wherein the location of the stimulus presented to the subject is adjusted based on the gaze direction measurement.

In an 11th aspect, a perimeter includes presenting a visual stimulus in visible wavelength together with a spatially coregistered stimulus presented in infrared waveband at a wavelength that is invisible to the eye, an imaging sensor configured to image the retina and capable of imaging in the wavelength of the infrared stimulus, and a registration unit capable of determining the location of the infrared stimulus on the retina.

In a 12th aspect, a method for imaging the retina through opaque or scattering ocular medium, wherein the image of the retina is recorded and an autocorrelation function of the image is calculated, and the autocorrelation function is used to reconstruct the original image or the retina with a higher resolution than the originally recorded image.

In a 13th aspect, perimeter wherein visual stimuli presented to the subject are less bright than the background on which they are presented.

In a 14th aspect, a method for reducing the visual field examination time, wherein the locations of the stimuli are determined based on known anatomy of the eye.

In a 15th aspect, a method of improving the accuracy of visual field examination, wherein the locations of the stimuli are determined during the examination based on the previous responses of the subject.

In a 16th aspect, a method of improving the accuracy of visual field examination, wherein the brightness of the stimuli are determined during the examination based on the previous responses of the subject.

In a 17th aspect, a method of describing the visual field examination results wherein the numerical values of visual field are interpolated at the locations between the measurement points.

In a 18th aspect, a method of presentation of the visual field examination results wherein the numerical values of visual field are interpolated in locations between the measurement points, and wherein the values of the visual field measurement at a plurality of selected interpolated points are presented to examiner.

In a 19th aspect, a method of presentation of the visual field examination results wherein the presented results are the probability of the detection of the visual stimulus as a function of the stimulus location and brightness.

In a 20th aspect, a method for determining the progression of the visual field loss wherein the input parameters for progression rate calculation is the set of probabilities of the detection of the stimulus as a function of the stimulus location and brightness.

In a 21st aspect, a method of visual field examination, and in particular a local sensitivity threshold evaluation wherein an OCT map of the retina is recorded and spatially registered to the visual field measurement device, and the starting brightness of the visual stimulus at every point is determined from the OCT evaluation of the thickness of the nerve fiber layer (NFL) or ganglion cell complex (GCC).

In a 22nd aspect, a system and method wherein the OCT data is spatially registered with the visual field examination data and wherein the visual field is presented on the screen for evaluation and the thickness of the retina nerve fiber layer at a single location or plurality of locations selected by the examiner may be presented on the screen for examination.

In a 23rd aspect, a system and method wherein the OCT data is spatially registered with the visual field examination data and wherein the visual field is presented on the display of a computing device for evaluation, and the examiner is capable of selecting a line or a plurality of lines passing over the visual field, and wherein the thickness of the retina nerve fiber layer may be displayed in a form of a graph or plurality of graphs on the display.

In a 24th aspect, a method wherein the damage to the optic nerve is assessed using an OCT image of the optic disk and wherein a perimetry examination is performed at a set of examination points predetermined based on the knowledge of anatomy and OCT image of the optic disk.

In a 25th aspect, a glaucoma diagnostic method wherein the retina nerve fiber layer is measured using an OCT device and the visual field is measured using a perimeter and wherein the two measurements are spatially registered and a cross-correlation function is calculated between the two fields and wherein two or more of the following: the color or grey scale coded OCT map of the RNFL, color or grey scale coded OCT map of the visual field, and color or grey scale coded OCT map of the correlation function is presented on the display of the computing device for evaluation.

In a 26th aspect, a glaucoma diagnostic method wherein the en-face OCT image is registered with the visual field examination and the visual field plot and a plot of a certain parameter from the en-face OCT image are simultaneously presented on the screen side by side or overlaying one another.

Figure 14:
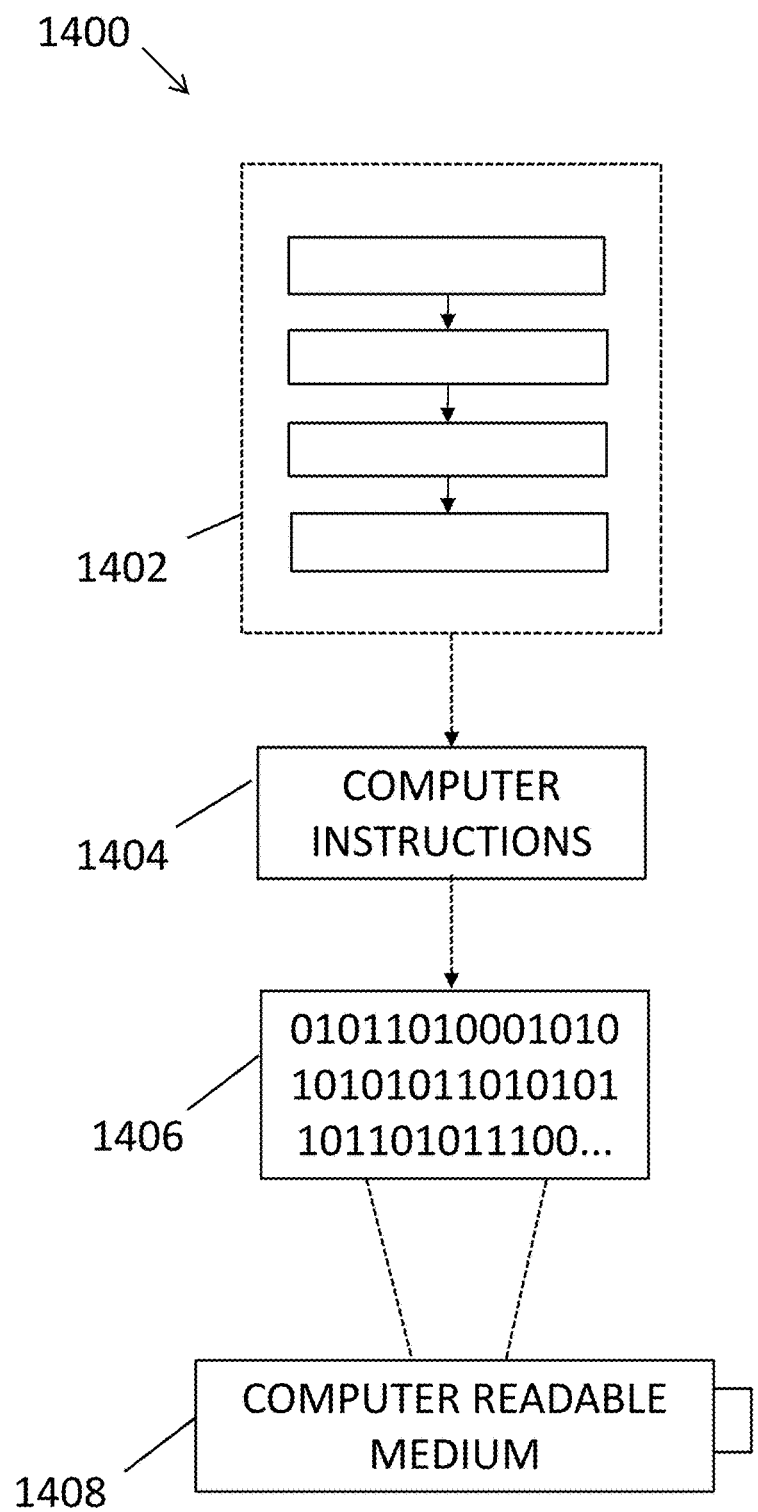
FIG. 14 is an illustration of an example computer-readable medium or computer-readable device including processor-executable instructions configured to embody one or more of the provisions set forth herein, according to one or more embodiments.

Still another embodiment involves a computer-readable medium including processor-executable instructions configured to implement one or more embodiments of the techniques presented herein. An embodiment of a computer-readable medium or a computer-readable device devised in these ways is illustrated in FIG. 14, wherein an implementation 1400 includes a computer-readable medium 1408, such as a CD-R, DVD-R, flash drive, a platter of a hard disk drive, etc., on which is encoded computer-readable data 1406. This computer-readable data 1406, such as binary data including a plurality of zero's and one's as shown in 1406, in turn includes a set of computer instructions 1404 configured to operate according to one or more of the principles set forth herein. In one such embodiment 1400, the processor-executable computer instructions 1404 may be configured to perform a method 1402, such as the method 600 of FIG. 6. In another embodiment, the processor-executable instructions 1404 may be configured to implement a system, such as the system 100 of FIG. 1 or the system 200 of FIG. 2. Many such computer-readable media may be devised by those of ordinary skill in the art that are configured to operate in accordance with the techniques presented herein.

As used in this application, the terms "component", "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, or a computer. By way of illustration, both an application running on a controller and the controller may be a component. One or more components residing within a process or thread of execution and a component may be localized on one computer or distributed between two or more computers.

Further, the claimed subject matter is implemented as a method, apparatus, or article of manufacture using standard programming or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, many modifications may be made to this configuration without departing from the scope or spirit of the claimed subject matter.

Figure 15:
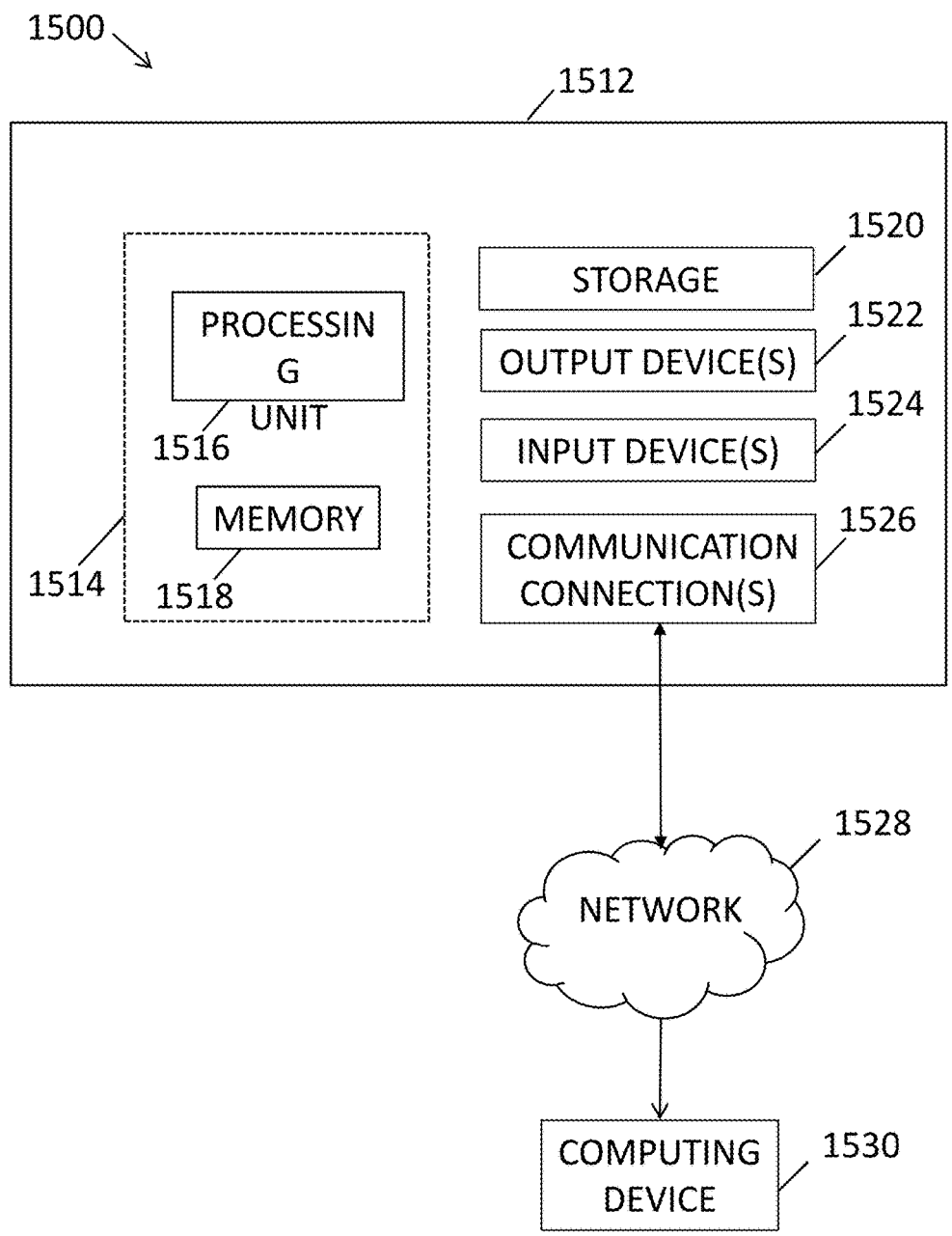
FIG. 15 is an illustration of an example computing environment where one or more of the provisions set forth herein are implemented, according to one or more embodiments.

FIG. 15 and the following discussion provide a description of a suitable computing environment to implement embodiments of one or more of the provisions set forth herein. The operating environment of FIG. 15 is merely one example of a suitable operating environment and is not intended to suggest any limitation as to the scope of use or functionality of the operating environment. Example computing devices include, but are not limited to, personal computers, server computers, hand-held or laptop devices, mobile devices, such as mobile phones, Personal Digital Assistants (PDAs), media players, and the like, multiprocessor systems, consumer electronics, mini computers, mainframe computers, distributed computing environments that include any of the above systems or devices, etc.

Generally, embodiments are described in the general context of "computer readable instructions" being executed by one or more computing devices. Computer readable instructions may be distributed via computer readable media as will be discussed below. Computer readable instructions may be implemented as program modules, such as functions, objects, Application Programming Interfaces (APIs), data structures, and the like, that perform one or more tasks or implement one or more abstract data types. Typically, the functionality of the computer readable instructions are combined or distributed as desired in various environments.

FIG. 15 illustrates a system 1500 including a computing device 1512 configured to implement one or more embodiments provided herein. In one configuration, computing device 1512 includes at least one processing unit 1516 and memory 1518. Depending on the exact configuration and type of computing device, memory 1518 may be volatile, such as RAM, non-volatile, such as ROM, flash memory, etc., or a combination of the two. This configuration is illustrated in FIG. 15 by dashed line 1514.

In other embodiments, device 1512 includes additional features or functionality. For example, device 1512 may include additional storage such as removable storage or non-removable storage, including, but not limited to, magnetic storage, optical storage, etc. Such additional storage is illustrated in FIG. 15 by storage 1520. In one or more embodiments, computer readable instructions to implement one or more embodiments provided herein are in storage 1520. Storage 1520 may store other computer readable instructions to implement an operating system, an application program, etc. Computer readable instructions may be loaded in memory 1518 for execution by processing unit 1516, for example.

The term "computer readable media" as used herein includes computer storage media. Computer storage media includes volatile and nonvolatile, removable and non-removable media implemented in any method or technology for storage of information such as computer readable instructions or other data. Memory 1518 and storage 1520 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which may be used to store the desired information and which may be accessed by device 1512. Any such computer storage media is part of device 1512.

The term "computer readable media" includes communication media. Communication media typically embodies computer readable instructions or other data in a "modulated data signal" such as a carrier wave or other transport mechanism and includes any information delivery media. The term "modulated data signal" includes a signal that has one or more of its characteristics set or changed in such a manner as to encode information in the signal.

Device 1512 includes input device(s) 1524 such as keyboard, mouse, pen, voice input device, touch input device, infrared cameras, video input devices, or any other input device. Output device(s) 1522 such as one or more displays, speakers, printers, or any other output device may be included with device 1512. Input device(s) 1524 and output device(s) 1522 may be connected to device 1512 via a wired connection, wireless connection, or any combination thereof. In one or more embodiments, an input device or an output device from another computing device may be used as input device(s) 1524 or output device(s) 1522 for computing device 1512. Device 1512 may include communication connection(s) 1526 to facilitate communications with one or more other devices 1530, such as through network 1528, for example.

Although the subject matter has been described in language specific to structural features or methodological acts, it is to be understood that the subject matter of the appended claims is not necessarily limited to the specific features or acts described above. Rather, the specific features and acts described above are disclosed as example embodiments.

Various operations of embodiments are provided herein. The order in which one or more or all of the operations are described should not be construed as to imply that these operations are necessarily order dependent. Alternative ordering will be appreciated based on this description. Further, not all operations may necessarily be present in each embodiment provided herein.

As used in this application, "or" is intended to mean an inclusive "or" rather than an exclusive "or". Further, an inclusive "or" may include any combination thereof (e.g., A, B, or any combination thereof). In addition, "a" and "an" as used in this application are generally construed to mean "one or more" unless specified otherwise or clear from context to be directed to a singular form. Additionally, at least one of A and B and/or the like generally means A or B or both A and B. Further, to the extent that "includes", "having", "has", "with", or variants thereof are used in either the detailed description or the claims, such terms are intended to be inclusive in a manner similar to the term "comprising".

Further, unless specified otherwise, "first", "second", or the like are not intended to imply a temporal aspect, a spatial aspect, an ordering, etc. Rather, such terms are merely used as identifiers, names, etc. for features, elements, items, etc. For example, a first channel and a second channel generally correspond to channel A and channel B or two different or two identical channels or the same channel. Additionally, "comprising", "comprises", "including", "includes", or the like generally means comprising or including, but not limited to.

It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A device for performing combined structure and function evaluation of a retina of a patient, comprising:
   a functional evaluation unit performing a visual examination by providing a visual stimulus to the retina and recording a reaction of the patient; and
   a structural evaluation unit recording one or more structural measurements associated with the retina of the patient,
   wherein the functional evaluation unit provides the visual stimulus to the retina based on an orientation of the RNFL bundles and previous responses from the patient to determine one or more scotoma boundaries.

2. The device of claim 1, wherein the functional evaluation unit determines progression of scotomas based on an area of a scotoma and movement of one or more of the scotoma boundaries.

3. A device for performing combined structure and function evaluation of a retina of a patient, comprising:
   a functional evaluation unit performing a visual examination by providing a visual stimulus to the retina and recording a reaction of the patient; and
   a structural evaluation unit recording one or more structural measurements associated with the retina of the patient,
   wherein the structural evaluation unit determines orientation of retinal nerve fiber layer (RNFL) bundles or RNFL capacity.

4. The device of claim 3, wherein the gaze tracking system tracks eyes of the patient using a retinal tracking system and an anterior segment tracking system.

5. The device of claim 3, wherein one of the two or more imaging sensors is an infrared camera or an anterior segment camera.

6. The device of claim 3, wherein during the visual examination, the functional evaluation unit projects:
   a fixation gaze target onto both eyes of the patient; and
   the visual stimuli onto merely one of the eyes of the patient at a time.

7. The device of claim 3, wherein the fixation gaze on the eye where stimuli is not projected appears on a dark background.

8. The device of claim 3, wherein the structural evaluation unit is a polarization sensitive optical coherence tomography (PS-OCT) unit, or a polarization sensitive scanning laser ophthalmoscope (PS-SLO).

9. The device of claim 3, wherein the functional evaluation unit provides the visual stimulus to the retina based on one or more of the structural measurements taken by the structural evaluation unit.

10. The device of claim 3, wherein the structural evaluation unit records one or more of the structural measurements based on the reaction of the patient to the visual stimulus, and wherein the location of the structural evaluation of the retina may be different from the location of the said functional evaluation of the retina.

11. The device of claim 10 wherein the correspondence between locations of the said structural and functional evaluations is determined by the orientation of the RNFL bundles.

12. The device of claim 3, wherein the functional evaluation unit provides the visual stimulus to the retina based on an orientation of the RNFL bundles and the results of the structural evaluation performed by the said device.

13. The device of claim 12, wherein the orientation of the RNFL bundles is determined by the structural measurement performed by the device.

14. The device of claim 12, wherein the orientation of the RNFL bundles is determined by a numerical modeling of RNFL propagation with input parameters to the said numerical model being one or more of the anatomical parameters of the eye that are relevant to the RNFL orientation.

15. The device of claim 12, wherein the orientation of the RNFL bundles is approximated from a normative database.

16. The device of claim 3, wherein the functional evaluation unit determines progression of a disease based on a change in the scotoma area and movement of one or more of the scotoma boundaries.

17. The device of claim 3, wherein one of the outputs of the said device is an index derived from a combination of the structural and functional evaluation performed by the structural and functional evaluation units of the said device.

18. The device of claim 17, wherein the said index may be a function of the location on the eye retina, and wherein the value of the index may differ from one portion of the retina to another.

* * * * *